(12) United States Patent
Taylor

(10) Patent No.: US 7,780,723 B2
(45) Date of Patent: Aug. 24, 2010

(54) HEART VALVE DELIVERY SYSTEM

(75) Inventor: David M. Taylor, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1022 days.

(21) Appl. No.: 11/152,288

(22) Filed: Jun. 13, 2005

(65) Prior Publication Data

US 2007/0005131 A1    Jan. 4, 2007

(51) Int. Cl.
*A61F 2/24* (2006.01)
*A61M 31/00* (2006.01)

(52) U.S. Cl. .................... 623/2.11; 604/95.04

(58) Field of Classification Search ............... 623/2.11, 623/1.11, 1.12, 900, 903, 904; 604/95.01, 604/95.04, 95.05, 171, 172, 510, 523–528, 604/530

See application file for complete search history.

(56) References Cited

U.S. PATENT DOCUMENTS

| | | | |
|---|---|---|---|
| 3,409,013 A | 11/1968 | Berry | |
| 3,587,115 A | 6/1971 | Shiley | |
| 3,671,979 A | 6/1972 | Moulopoulos | |
| 4,056,854 A | 11/1977 | Boretos et al. | |
| 4,586,923 A * | 5/1986 | Gould et al. ............. | 604/95.04 |
| 4,592,340 A | 6/1986 | Boyles | |
| 4,733,665 A | 3/1988 | Palmaz | |
| 4,777,951 A | 10/1988 | Cribier et al. | |
| 4,787,899 A | 11/1988 | Lazarus | |
| 4,796,629 A | 1/1989 | Grayzel | |
| 5,059,177 A | 10/1991 | Towne et al. | |
| 5,085,635 A | 2/1992 | Cragg | |
| 5,089,015 A | 2/1992 | Ross | |
| 5,167,628 A | 12/1992 | Boyles | |
| 5,332,402 A | 7/1994 | Teitelbaum | |
| 5,370,685 A | 12/1994 | Stevens | |
| 5,397,351 A | 3/1995 | Pavcnik et al. | |
| 5,411,552 A | 5/1995 | Andersen et al. | |
| 5,545,209 A | 8/1996 | Roberts et al. | |
| 5,554,185 A | 9/1996 | Block et al. | |

(Continued)

FOREIGN PATENT DOCUMENTS

EP    1 057460    12/2000

(Continued)

OTHER PUBLICATIONS

International Search Report for PCT/US2006/022540.

*Primary Examiner*—Nicholas D Lucchesi
*Assistant Examiner*—Nathan R Price
(74) *Attorney, Agent, or Firm*—David L. Hauser

(57) ABSTRACT

A delivery system for delivering a prosthetic heart valve to a native valve site within the human vasculature. The prosthetic valve is disposed on a balloon at the end of a balloon catheter. The balloon catheter passes through a delivery sleeve assembly and handle. A pull wire travels from the handle to a distal end of the delivery sleeve assembly. Actuation of the handle pulls on the pull wire, which causes openings in a slotted tube of the delivery sleeve assembly to close, thus causing the delivery sleeve assembly to bend. A stretchable cover is placed over the slotted tube for biasing the steerable catheter toward a straight position. Once advanced to the native valve site, the prosthetic valve is deployed by inflating the balloon.

10 Claims, 24 Drawing Sheets

U.S. PATENT DOCUMENTS

| | | | |
|---|---|---|---|
| 5,591,195 | A | 1/1997 | Taheri et al. |
| 5,599,305 | A * | 2/1997 | Hermann et al. ......... 604/95.04 |
| 5,702,368 | A | 12/1997 | Stevens et al. |
| 5,749,890 | A | 5/1998 | Shaknovich |
| 5,782,809 | A | 7/1998 | Umeno et al. |
| 5,855,597 | A | 1/1999 | Jayaraman |
| 5,855,601 | A | 1/1999 | Bessler et al. |
| 5,925,063 | A | 7/1999 | Khosravi |
| 5,957,949 | A | 9/1999 | Leonhardt et al. |
| 5,968,068 | A | 10/1999 | Dehdashtian et al. |
| 6,042,589 | A | 3/2000 | Marianne |
| 6,059,809 | A | 5/2000 | Amor et al. |
| 6,162,208 | A | 12/2000 | Hipps |
| 6,168,614 | B1 | 1/2001 | Andersen et al. |
| 6,245,102 | B1 | 6/2001 | Jayaraman |
| 6,299,637 | B1 | 10/2001 | Shaolia et al. |
| 6,302,906 | B1 | 10/2001 | Goicoechea et al. |
| 6,383,171 | B1 * | 5/2002 | Gifford et al. ............... 604/508 |
| 6,425,916 | B1 | 7/2002 | Garrison et al. |
| 6,454,799 | B1 | 9/2002 | Schreck |
| 6,458,153 | B1 | 10/2002 | Bailey et al. |
| 6,569,196 | B1 | 5/2003 | Vesely |
| 6,605,112 | B1 | 8/2003 | Moll et al. |
| 6,656,213 | B2 | 12/2003 | Solem |
| 6,730,118 | B2 | 5/2004 | Spenser et al. |
| 6,769,434 | B2 | 8/2004 | Liddicoat |
| 6,786,925 | B1 | 9/2004 | Schoon |
| 6,790,229 | B1 | 9/2004 | Berreklouw |
| 6,797,002 | B2 | 9/2004 | Spence |
| 6,821,297 | B2 | 11/2004 | Snyders |
| 6,830,584 | B1 | 12/2004 | Seguin |
| 6,830,585 | B1 | 12/2004 | Artof |
| 6,866,650 | B2 | 3/2005 | Stevens |
| 6,872,223 | B2 | 3/2005 | Roberts |
| 6,893,460 | B2 | 5/2005 | Spenser et al. |
| 6,908,481 | B2 | 6/2005 | Cribier |
| 6,951,571 | B1 | 10/2005 | Srivastava |
| 6,989,028 | B2 | 1/2006 | Lashinski et al. |
| 7,147,663 | B1 | 12/2006 | Berg et al. |
| 2001/0002445 | A1 | 5/2001 | Vesely |
| 2001/0007956 | A1 | 7/2001 | Letac et al. |
| 2002/0029014 | A1 | 3/2002 | Jayaraman |
| 2002/0032481 | A1 | 3/2002 | Gabbay |
| 2002/0138138 | A1 | 9/2002 | Yang |
| 2003/0050694 | A1 | 3/2003 | Yang et al. |
| 2003/0065386 | A1 | 4/2003 | Weadock |
| 2003/0069492 | A1 | 4/2003 | Abrams et al. |
| 2003/0109924 | A1 | 6/2003 | Cribier |
| 2003/0199963 | A1 | 10/2003 | Tower et al. |
| 2003/0212410 | A1 | 11/2003 | Stenzel et al. |
| 2004/0039436 | A1 | 2/2004 | Spenser et al. |
| 2004/0093060 | A1 | 5/2004 | Sequin et al. |
| 2004/0097788 | A1 | 5/2004 | Mourles et al. |
| 2004/0111096 | A1 | 6/2004 | Tu |
| 2004/0122516 | A1 | 6/2004 | Fogarty |
| 2004/0167573 | A1 | 8/2004 | Williamson |
| 2004/0167620 | A1 | 8/2004 | Ortiz |
| 2004/0186563 | A1 | 9/2004 | Lobbi |
| 2004/0193261 | A1 | 9/2004 | Berreklouw |
| 2004/0210304 | A1 | 10/2004 | Seguin et al. |
| 2004/0210307 | A1 | 10/2004 | Khairkhahan |
| 2004/0215333 | A1 | 10/2004 | Duran |
| 2004/0225353 | A1 | 11/2004 | McGuckin, Jr. |
| 2004/0225354 | A1 | 11/2004 | Allen |
| 2004/0254636 | A1 | 12/2004 | Flagle et al. |
| 2004/0260394 | A1 | 12/2004 | Douk et al. |
| 2005/0010287 | A1 | 1/2005 | Macoviak |
| 2005/0033398 | A1 | 2/2005 | Seguin |
| 2005/0043790 | A1 | 2/2005 | Seguin |
| 2005/0049692 | A1 | 3/2005 | Numamoto |
| 2005/0049696 | A1 | 3/2005 | Siess |
| 2005/0060029 | A1 | 3/2005 | Le |
| 2005/0075584 | A1 | 4/2005 | Cali |
| 2005/0075712 | A1 | 4/2005 | Biancucci |
| 2005/0075717 | A1 | 4/2005 | Nguyen |
| 2005/0075719 | A1 | 4/2005 | Bergheim |
| 2005/0075724 | A1 | 4/2005 | Svanidze |
| 2005/0075730 | A1 | 4/2005 | Myers |
| 2005/0075731 | A1 | 4/2005 | Artof |
| 2005/0096738 | A1 | 5/2005 | Cali |
| 2005/0107871 | A1 | 5/2005 | Realyvasquez et al. |
| 2005/0113910 | A1 | 5/2005 | Paniagua |
| 2005/0131438 | A1 | 6/2005 | Cohn |
| 2005/0137686 | A1 | 6/2005 | Salahieh |
| 2005/0137692 | A1 | 6/2005 | Haug |
| 2005/0137695 | A1 | 6/2005 | Salahieh |
| 2005/0137701 | A1 | 6/2005 | Salahieh |
| 2005/0143809 | A1 | 6/2005 | Salahieh |
| 2005/0187616 | A1 | 8/2005 | Realyvasquez |
| 2005/0203549 | A1 | 9/2005 | Realyvasquez |
| 2005/0203618 | A1 | 9/2005 | Sharkawy |
| 2005/0222674 | A1 | 10/2005 | Paine |
| 2005/0228495 | A1 | 10/2005 | Macoviak |
| 2005/0234546 | A1 | 10/2005 | Nugent |
| 2005/0240200 | A1 | 10/2005 | Bergheim |
| 2006/0004439 | A1 | 1/2006 | Spenser et al. |
| 2006/0009841 | A1 | 1/2006 | McGuckin et al. |
| 2006/0259134 | A1 | 11/2006 | Schwammenthal et al. |
| 2007/0027518 | A1 | 1/2007 | Herrmann et al. |
| 2007/0016286 | A1 | 2/2007 | Case et al. |
| 2007/0088431 | A1 | 4/2007 | Bourang |

FOREIGN PATENT DOCUMENTS

| | | |
|---|---|---|
| WO | WO94/03227 | 2/1994 |
| WO | WO 99/12483 | 3/1999 |
| WO | WO 02/060352 | 8/2002 |
| WO | WO 03/030776 | 4/2003 |
| WO | WO 2005/004753 | 1/2005 |
| WO | WO 2005/046528 | 5/2005 |

* cited by examiner

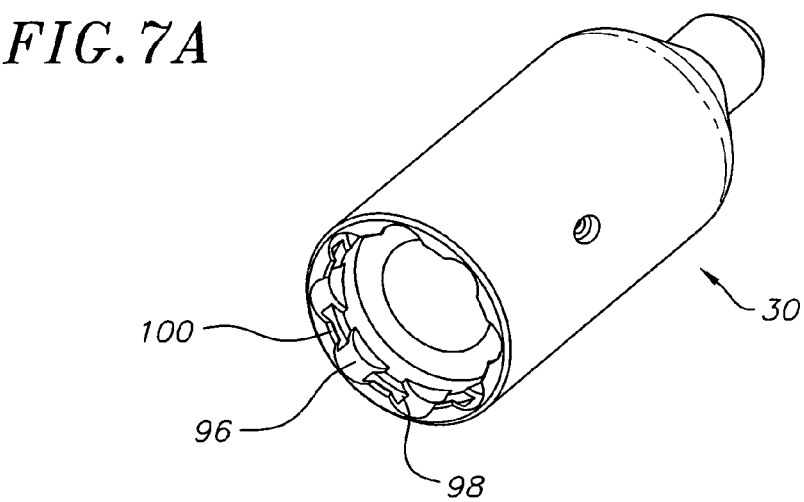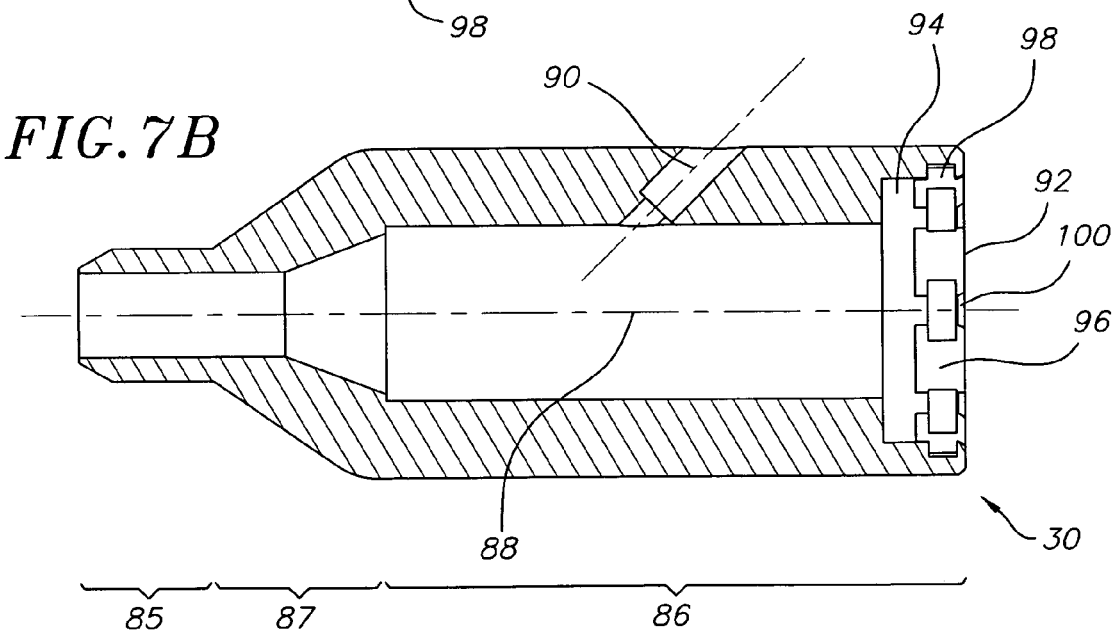

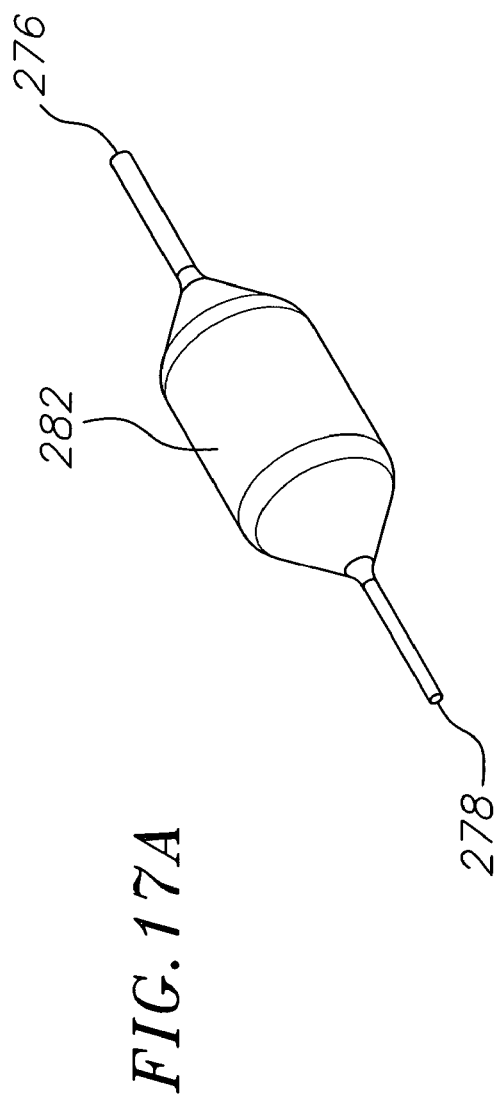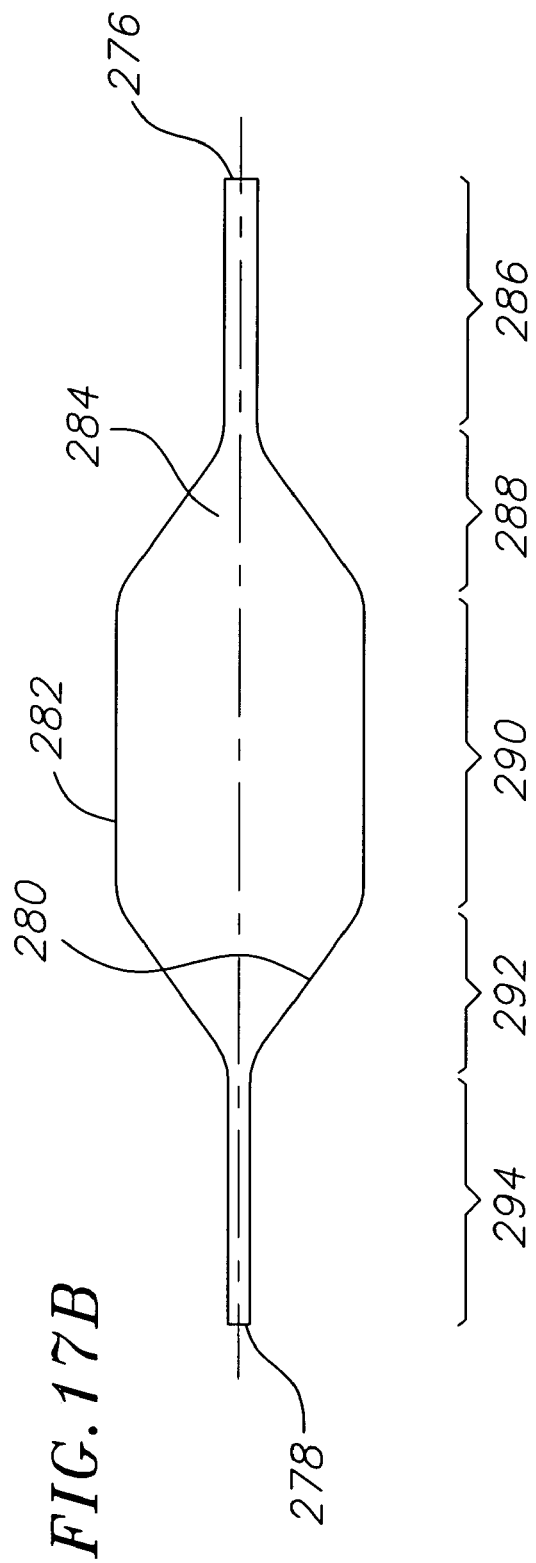
FIG. 17A
FIG. 17B

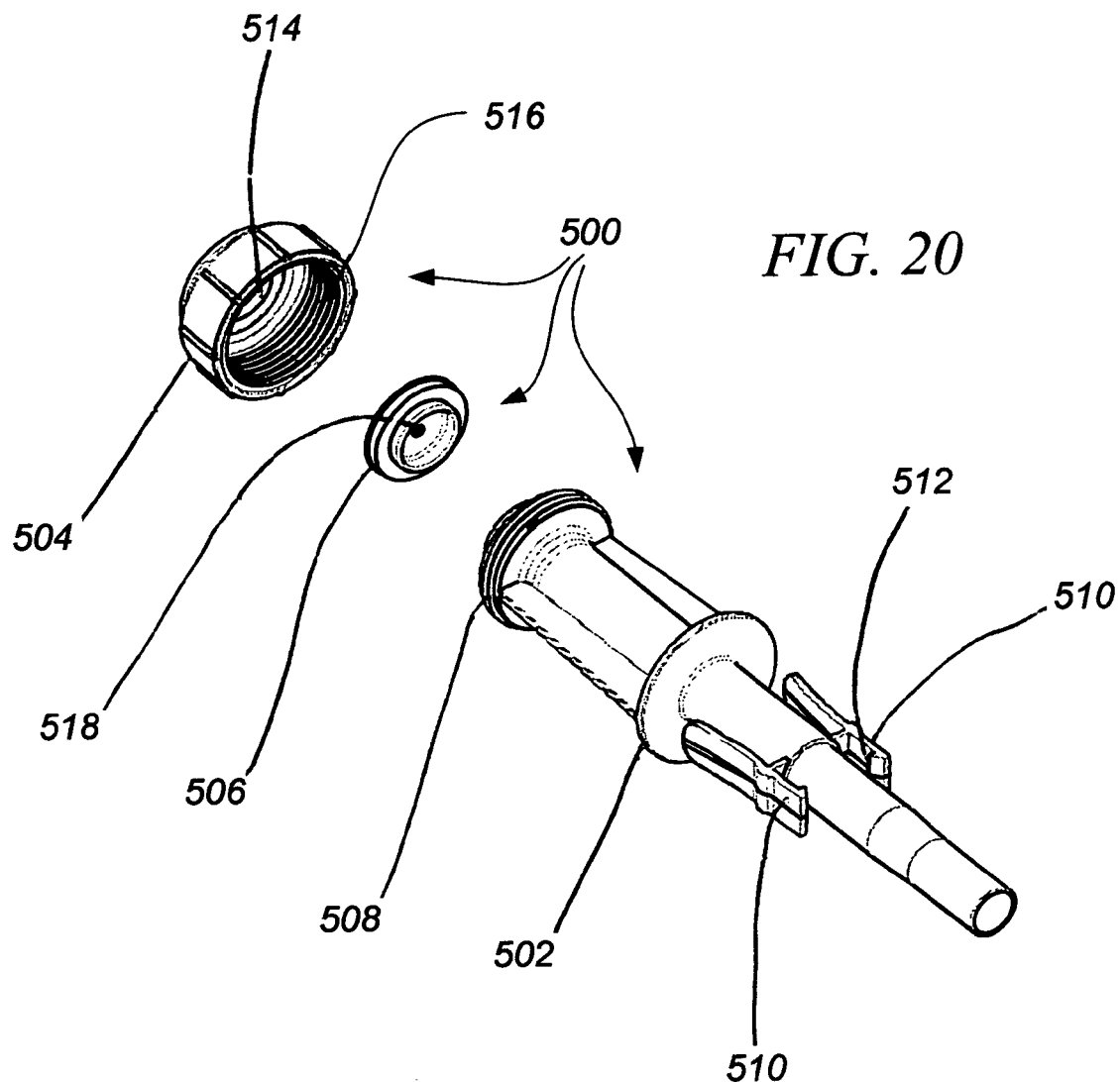

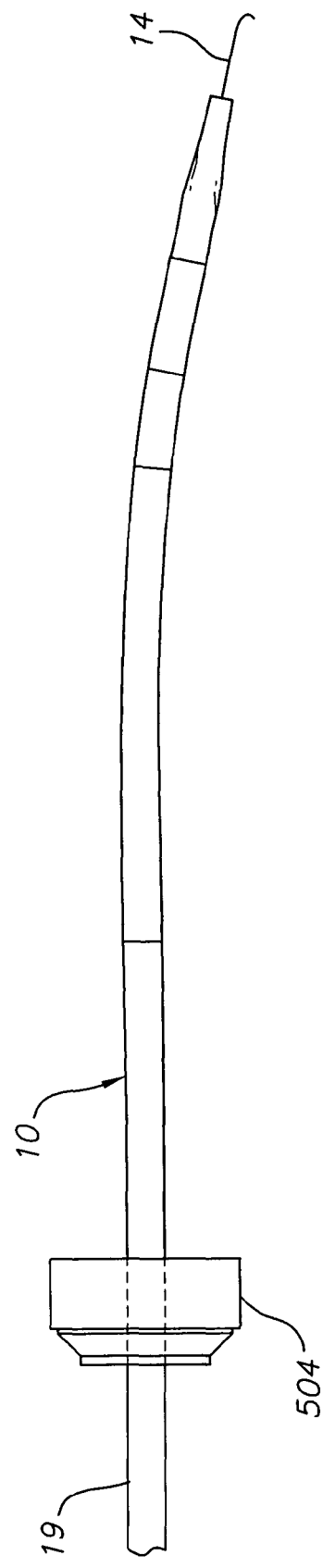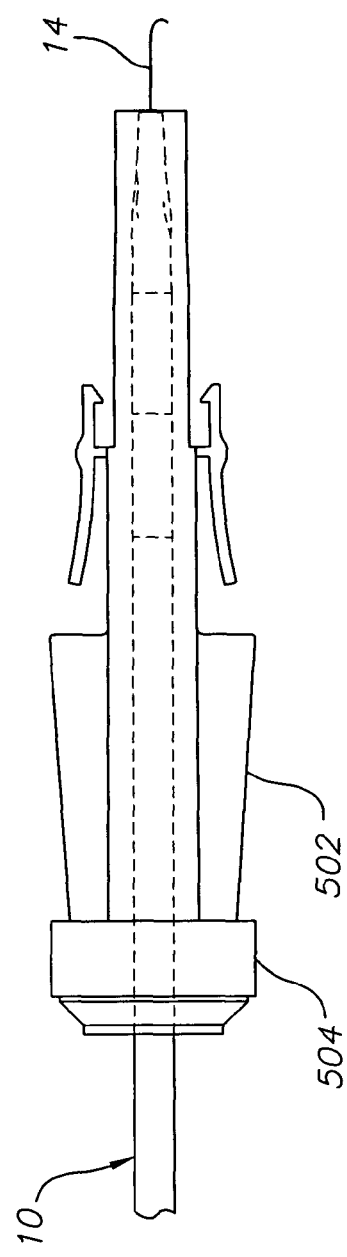

HEART VALVE DELIVERY SYSTEM

BACKGROUND OF THE INVENTION

The present invention relates to systems used to deliver a prosthetic valve to a heart. More specifically, the present invention is directed to an improved steerable delivery system for delivery of a prosthetic valve to a human heart.

Catheters are known in the art and have been commonly used to reach locations inside the body that are not readily accessible by surgery or where access without surgery is desirable. The usefulness of catheters is largely limited by the ability of the catheter to successfully navigate through small vessels and around tight bends, such as around the aortic arch.

Over the years, a variety of steerable catheters have been proposed for facilitating navigation through difficult vasculature. For example, some known devices employ a series of connected segments, each comprising a shape which allows the catheter to form a bent configuration adaptable to fit the particular need. The use of many connected segments, however, is complicated and costly.

Also known in the art is a device wherein portions have been removed from a hollow stylet wire, thus allowing the hollow wire to bend in areas where portions have been removed. However, known devices of this type are used as stylets and have not been adapted for use in a steerable catheter.

Also known in the art is a device wherein spring bands are employed into a steerable catheter, wherein one spring band has a natural curvature opposite that of the direction of the bending of the device, thus providing stability to the device. However, these bands add unnecessary complexity to the device and are therefore undesirable for many uses.

Although a variety of bendable and steerable devices have been proposed over the years, each of the existing devices has shortcomings that limit its effectiveness. Accordingly, an urgent need exists for an improved steerable delivery system to facilitate advancement of an implant and/or therapy device through a patient's vasculature to a treatment site. It is desirable that such a system overcomes the shortcomings associated with existing devices. It is also desirable that such a system be versatile, reliable and easy to use. The present invention addresses this need.

SUMMARY OF THE INVENTION

Preferred embodiments of the present invention provide a heart valve delivery system for delivery of a prosthetic (i.e., replacement) heart valve to a native valve site within the human vasculature. The delivery system includes a delivery sleeve assembly having a steerable section for facilitating navigation around bends. The system is well suited for advancing a prosthetic valve through the aorta (i.e., in a retrograde approach) for replacing a stenotic aortic valve.

In one preferred embodiment, the heart valve delivery system comprises a tubular sleeve, a selectively steerable section coupled to a distal end of the sleeve, an elongate balloon catheter extending through the sleeve and steerable section, and a prosthetic valve disposed over an expandable balloon along a distal end portion of the elongate balloon catheter. The sleeve, steerable section, balloon catheter and prosthetic valve are configured for advancement as a single unit through a patient's vasculature. During advancement, the prosthetic valve is located adjacent to a distal end portion of the steerable section and may be advanced therefrom if desired.

In one variation, the sleeve of the heart valve delivery system comprises first and second outer lumens extending along a side of the sleeve. A pull wire passes through the first outer lumen, through the steerable section to the distal end portion of the steerable section, and returns through the steerable section and through the second outer lumen. The pull wire is preferably actuated by a rotational handle assembly, wherein the rotational handle assembly is located proximal to the sleeve.

In another variation, the steerable section comprises a slotted tube having a first straight position and a second curved position. The steerable section may be formed, at least in part, of a stainless steel hypotube. In one preferred embodiment, the sleeve is formed of a polyether block amide, known as Pebax®, and comprises a soft durometer Pebax® near a distal end thereof.

The prosthetic valve may be located distal to the steerable section such that the distal end portion of the steerable section abuts a proximal end of the prosthetic valve. Alternatively, a shroud may be coupled to the distal end portion of the steerable section. The shroud surrounds at least a portion of the prosthetic valve during advancement through the patient's vasculature.

In another embodiment, a heart valve delivery system comprises a delivery sleeve assembly having a main lumen, a slotted tube forming a steerable section of the delivery sleeve assembly, the steerable section having a first configuration wherein the steerable section is substantially straight and a second configuration wherein the steerable section is curved. The steerable section is enveloped by a covering, wherein the covering is stretchable such that it biases the steerable section from the second configuration to the first configuration. An elongate balloon catheter extends through the main lumen of the delivery sleeve assembly and a prosthetic valve is mounted to a balloon located at a distal end of the balloon catheter. The steerable section is preferably acted upon by a pull wire which is actuated by a rotator handle which is mounted to a proximal end of the delivery sleeve assembly. The covering is preferably formed with a soft durometer polyether block amide known as Pebax®. The sleeve is preferably formed of a polyether block amide and comprises a soft durometer polyether block amide near a distal end thereof.

In another embodiment, a method of delivering a prosthetic valve to a native valve site of a patient involves disposing a prosthetic valve over a balloon on a balloon catheter and placing the balloon catheter inside a delivery sleeve assembly having a steerable section which is actuated by a pull wire running along the length of the delivery sleeve assembly and attached to a moving member of a handle. The prosthetic valve is advanced to the native valve site by pushing the valve through iliac and femoral arteries of the patient, over an aortic arch, and to the native valve site, whereby the moving member pulls the pull wire when the handle is rotated in a first direction, causing the steerable section to bend, and whereby the moving member releases the pull wire when the handle is rotated in a second direction, allowing the rigidity of the delivery sleeve assembly to straighten the steerable section. After reaching the native valve site, the balloon is inflated to deploy the prosthetic valve.

In one variation, the prosthetic valve is pushed through stenotic leaflets of an aortic valve site while the steerable section is bent. In another variation, the balloon catheter is distally advanced relative to the delivery sleeve assembly until the prosthetic valve is located within the native valve site. The prosthetic valve preferably comprises a stent portion supporting a valve structure. Because the delivery sleeve assembly provides steerability, an outer surface of the stent may be substantially exposed during advancement over the aortic arch without damaging the aorta. For enhanced pushability, a distal end of the steerable section preferably abuts a proximal end of the stent portion while advancing the prosthetic valve to the native valve site.

In yet another embodiment, a method of delivering a prosthetic valve to a native valve site comprises disposing an expandable prosthetic valve over a balloon along a distal end portion of a balloon catheter, placing the balloon catheter inside a delivery sleeve assembly having a steerable section which is actuated by a pull wire and advancing the prosthetic valve and delivery sleeve assembly toward the native valve site substantially as a single unit while selectively adjusting the curvature of the steerable section to facilitate advancement. When the prosthetic valve is advanced using a retrograde approach (i.e., over the aortic arch), the prosthetic valve may be advanced out of the delivery sleeve assembly after navigating the aortic arch. More particularly, the prosthetic valve may be advanced from the delivery sleeve assembly into the native valve site. The balloon is inflated for deploying the expandable prosthetic valve.

BRIEF DESCRIPTION OF THE DRAWINGS

Features and advantages of the present invention will become appreciated as the same become better understood with reference to the specification, claims, and appended drawings wherein:

FIGS. 7A and 7B are perspective and cross sectional views, respectively, of a hub which is disposed around the second core member;

FIGS. 17A and 17B are perspective and cross sectional views, respectively, of a balloon which forms a portion of the balloon catheter of FIG. 16;

FIGS. 18A and 18B are cross sectional views of a distal end of the delivery system, wherein FIG. 18A illustrates a first embodiment with the prosthetic heart valve disposed distal to the shroud and FIG. 18B shows a second embodiment with the prosthetic heart valve disposed within the shroud;

FIG. 20 is an exploded perspective view of a loader assembly used for loading the balloon catheter and prosthetic valve into the introducer sheath assembly;

FIGS. 21A and 21B are side views illustrating the insertion of the delivery system into the loader assembly;

DETAILED DESCRIPTION OF THE PREFERRED EMBODIMENTS

Figure 1:
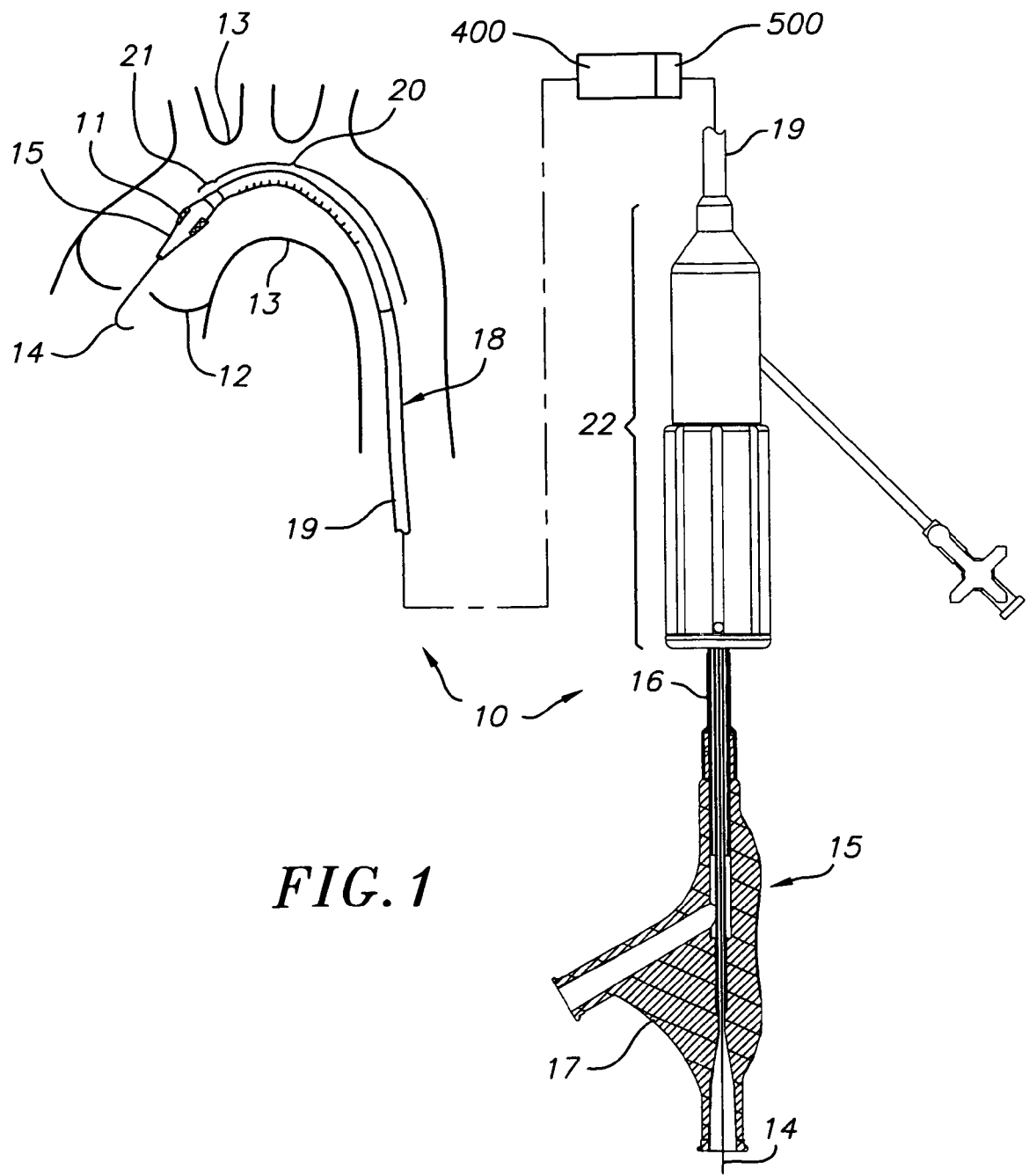
FIG. 1 is a side view of the heart valve delivery system delivering a heart valve to a native valve site according one preferred embodiment of the present invention.

With reference now to FIG. 1, for purposes of illustration, one preferred embodiment of a heart valve delivery system 10 for delivering a prosthetic valve 11 to a diseased aortic valve 12 of a human heart is shown. The delivery system is well-suited for delivering the prosthetic valve 11 through a patient's vasculature and over an aortic arch 13 to a location adjacent the diseased valve 12.

The delivery system 10 generally includes a guide wire 14 and a balloon catheter 15 configured for advancement over the guide wire 14. The prosthetic valve 11 is provided along the distal end portion of the balloon catheter. The balloon catheter 15 includes a tubular section 16 and a handle/support 17 at a proximal end of the tubular section 16. The tubular section 16 of the balloon catheter 15 is received within a delivery sleeve assembly 18. The delivery sleeve assembly generally comprises a sleeve 19, a steerable section 20 and a shroud section 21. A proximal end of the delivery sleeve assembly 18 is mounted to a handle 22. The delivery system 10 passes through an introducer sheath assembly 400 and a loader assembly 500, both of which will be described in more detail below, to enter the body vessel and deliver the valve 11.

Figure 2:
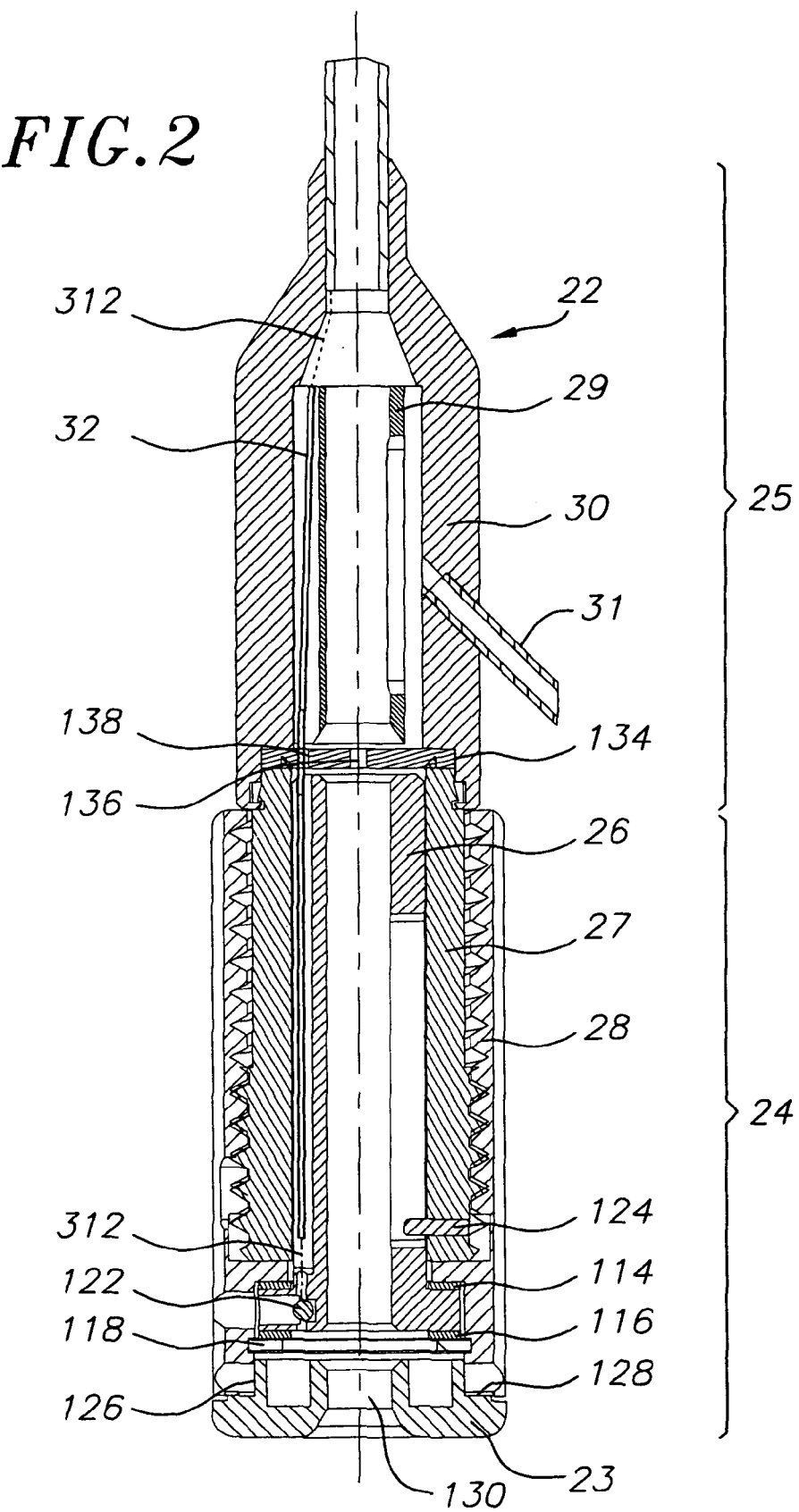
FIG. 2 is a cross sectional view of a handle used in the delivery system.

With reference to FIG. 2, the handle 22 at the proximal end of the delivery sleeve assembly 18 generally includes an end cap 23, an adjustable portion 24, and a hemostasis portion 25. The adjustable portion 24 includes a first core member 26, a partially threaded member 27 around the first core member 26, and a rotator handle 28 around the partially threaded member 27. The hemostasis portion 25 includes a second core member 29 and a hub 30 around the second core member 29. A hemostasis tube 31 extends outwards from the hub 30. A guide tube 32 is placed within the handle 22 as will be described in greater detail below.

Figure 3A:
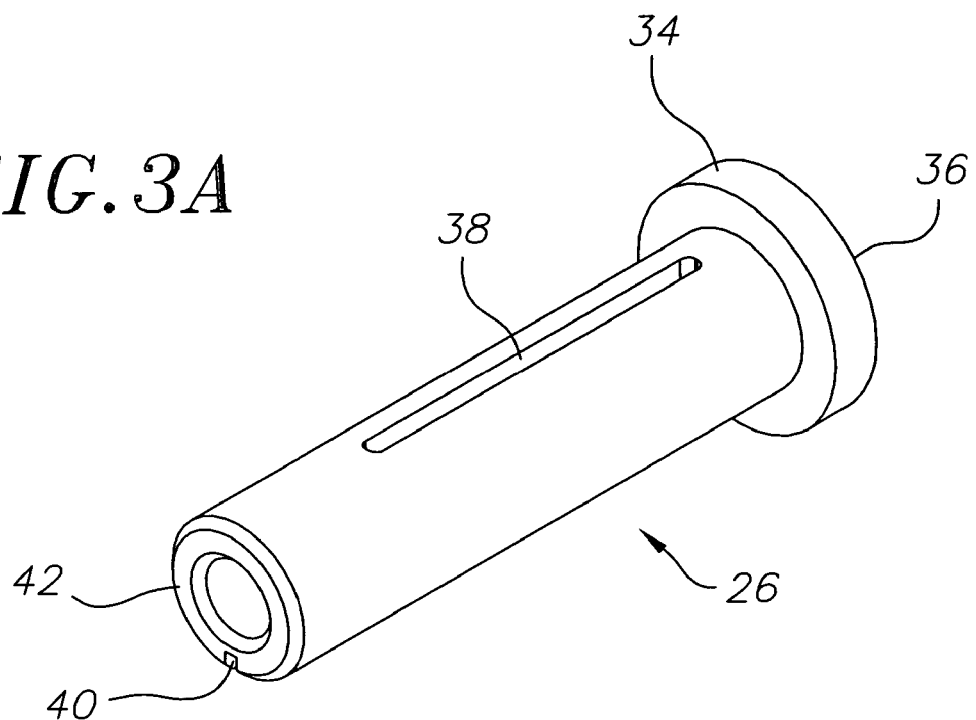
FIGS. 3A and 3B are perspective and cross sectional views, respectively, of a first core member which forms a portion of the handle.
Figure 3B:
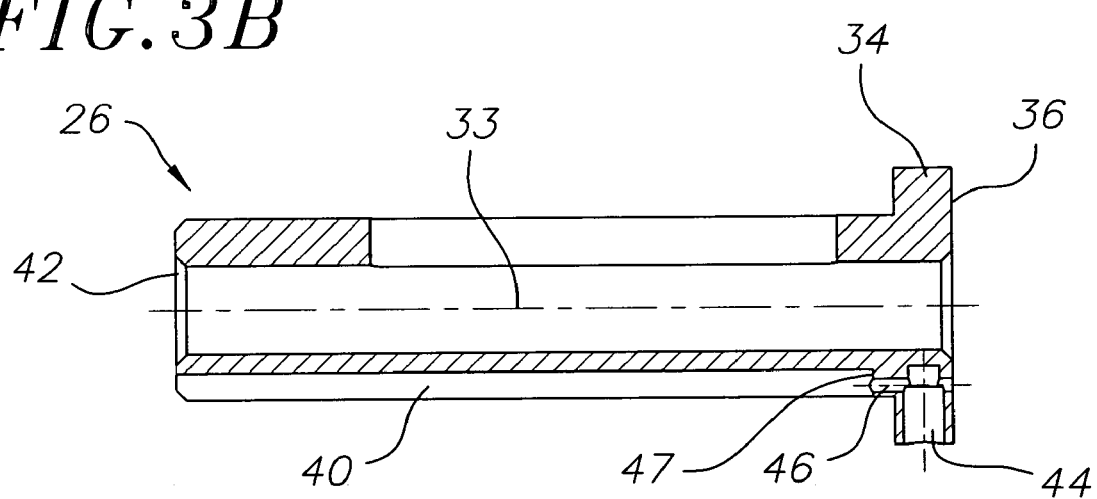

With reference to FIGS. 3A and 3B, the first core member 26 is generally tube shaped having a passageway 33 extending longitudinally therethrough. An annular flange 34 forms a proximal end 36 of the first core member 26. A first slot opening 38 allows communication from the outer surface of the first core member 26 into the passageway 33, and along a length of the first core member 26. A second slot 40 travels along the length of the outer surface of the first core member 26 from a distal end 42 towards the flange 34. The flange 34 includes a first fastener opening 44 extending radially from the outer surface of the first core member 26. A longitudinally extending access opening 46 at a proximal end of the slot 40 extends from a proximal end wall 47 of the slot 40 into the first fastener opening 44.

Figure 4A:
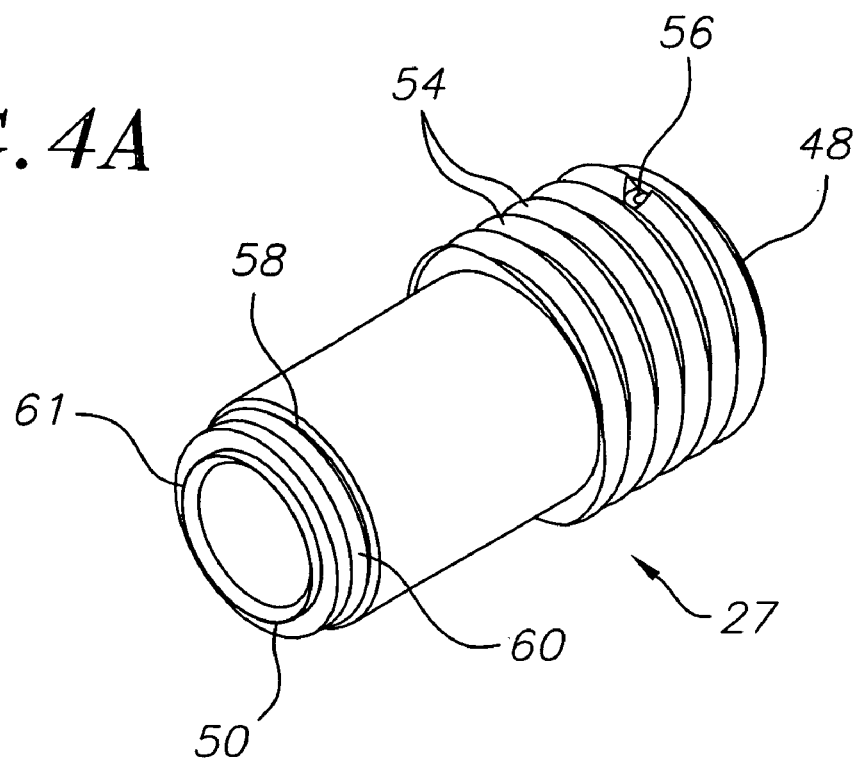
FIGS. 4A and 4B are perspective and cross sectional view, respectively, of a partially threaded member which is disposed around the core member.
Figure 4B:
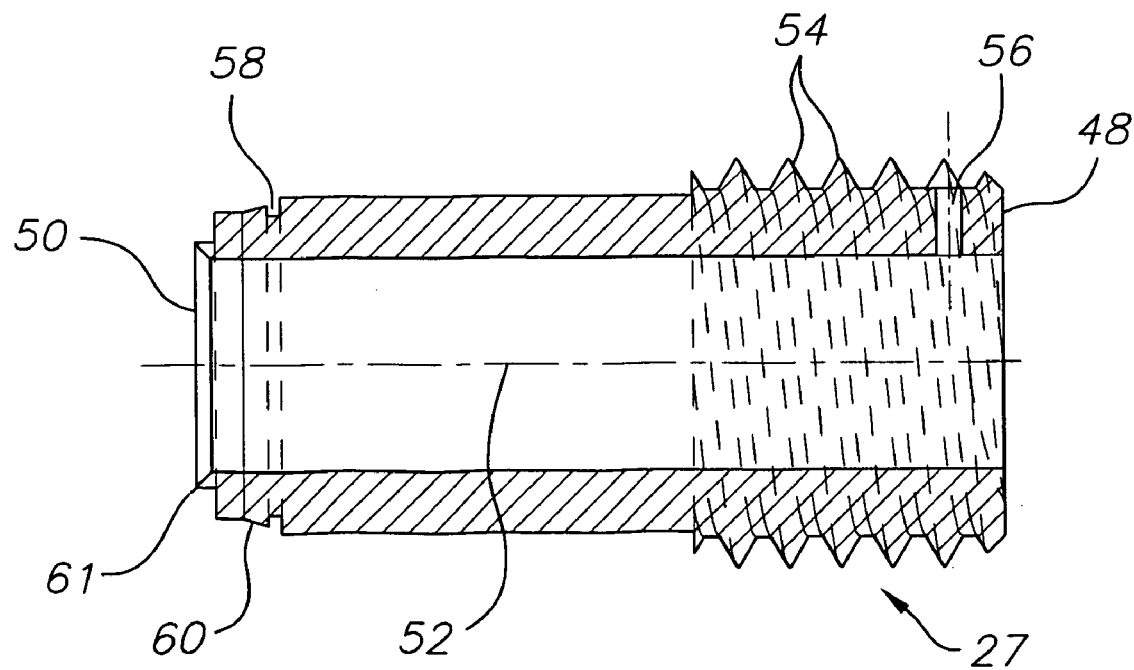

With reference to FIGS. 4A and 4B, the partially threaded member 27 has a proximal end 48 and a distal end 50. The partially threaded member 27 is generally tube shaped having a passageway 52 extending longitudinally therethrough. Toward the proximal end 48, the outer surface of the partially threaded member 27 has an exterior thread 54. The thread 54 includes a radially extending dowel opening 56 extending into the passageway 52 of the partially threaded member 27. Toward the distal end 50, the outer surface of the partially threaded member 27 forms an annularly shaped groove 58. The outer surface of the partially threaded member 27 also forms a tapered surface 60, located distally adjacent to the annularly shaped groove 58, toward the distal end 50. A pointed annular tip 61 forms the distal end 50 of the partially threaded member 27.

Figure 5A:
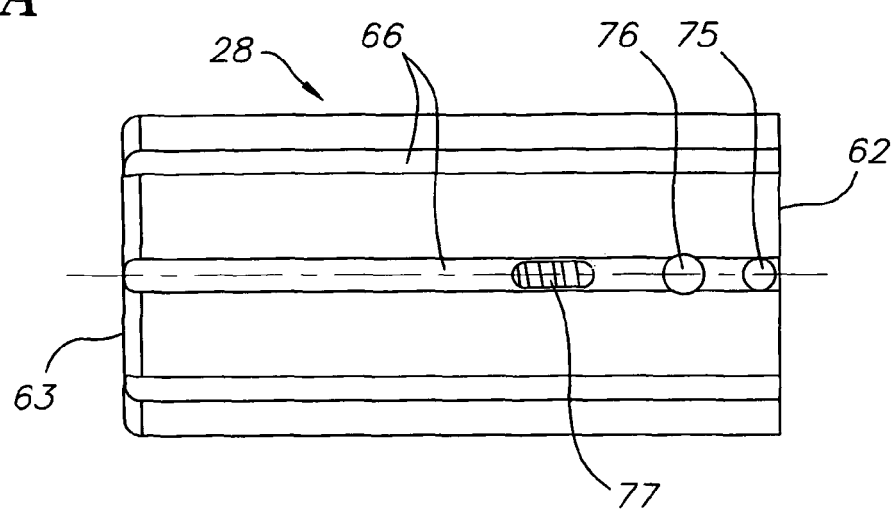
FIGS. 5A and 5B are side and cross sectional views, respectively, of a rotator handle.
Figure 5B:
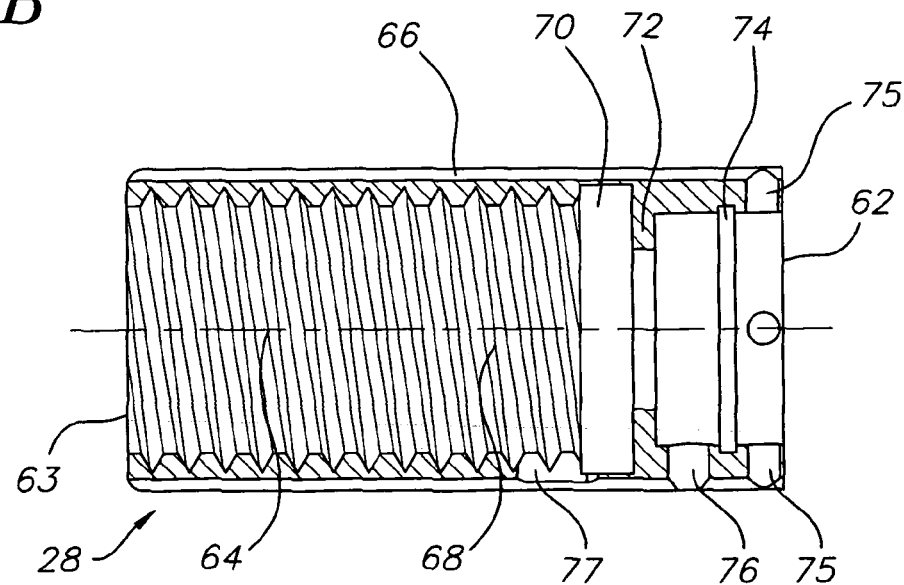

With reference to FIGS. 5A and 5B, the rotator handle 28 preferably comprises an elongated cylinder having a proximal end 62 and a distal end 63 and includes a passageway 64 extending longitudinally therethrough. On its outer surface, the rotator handle 28 includes grooved portions 66 extending along its length. On its inner surface, the rotator handle 28 includes a threaded portion 68 that extends inwardly from the distal end 63, a first annularly shaped recess 70 proximally adjacent the threaded portion 68, an annular flange 72 adjacent the first annularly shaped recess 70 extending inwardly from the inner surface, and a second annularly shaped recess 74 adjacent the proximal end 62 of the rotator handle 28. Fastener openings 75 pass from the outer surface to the inner surface of the rotator handle 28 in the area of the passageway 64 located proximally adjacent the second annularly shaped recess 74 distally adjacent the proximal end 62 of the rotator handle 28. An access opening 76 passes from the outer surface to the inner surface of the rotator handle 28 in the area of the passageway 64 distally adjacent the second annularly shaped recess 74 and proximally adjacent the annularly shaped flange 72. A second access opening 77 also extends from the outer surface to the inner surface of the rotator handle 28 at a proximal end of the threaded portion 68.

Figure 6A:
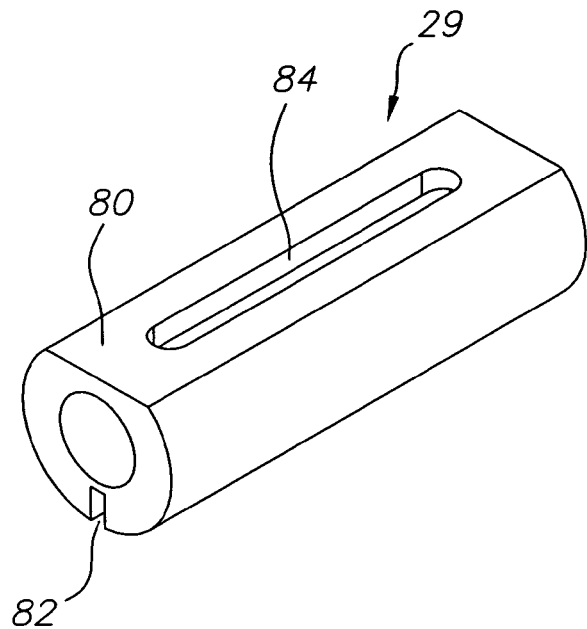
FIGS. 6A and 6B are perspective and cross sectional views, respectively, of a second core member which forms another portion of the handle.
Figure 6B:
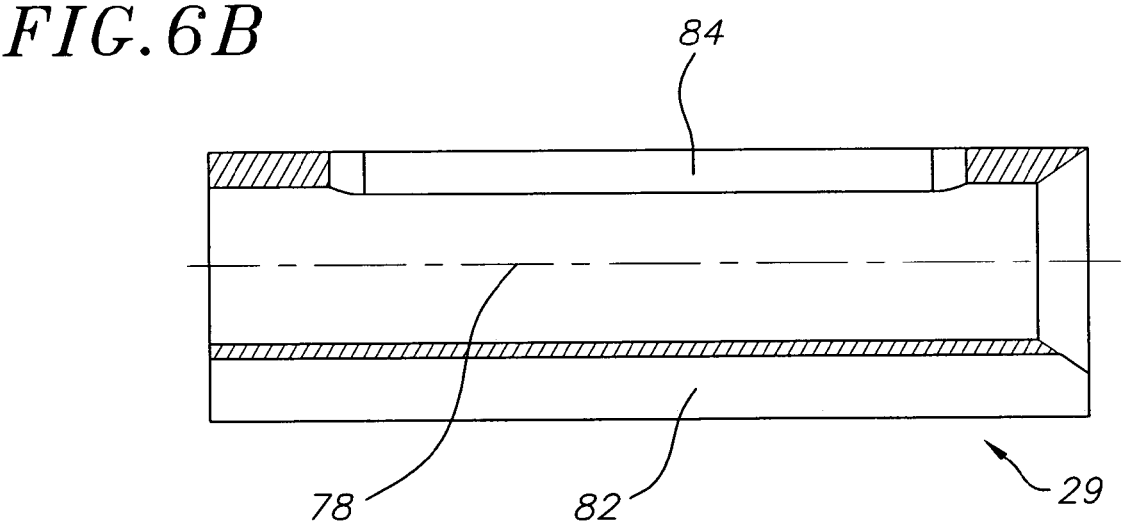

With reference to FIGS. 6A and 6B, the second core member 29 is generally tube shaped and includes a passageway 78 extending therethrough. A flat portion 80 of the second core member 29 further defines its outer surface. The outer surface of the second core member 29 includes a slot 82 which travels longitudinally along its length. The second core member 29 also includes a longitudinally extending slot 84 passing through the flat portion 80 of the outer surface into the passageway 78 of the second core member 29.

With reference to FIGS. 7A and 7B, the hub 30 is formed by first and second cylindrical sections 85, 86 connected by a tapered section 87. A passageway 88 extends through the hub 30. The passageway 88 increases in size in the tapered section 87 while transitioning from the first cylindrical section 85 to the second cylindrical section 86. A hemostasis valve opening 90 extends diagonally from an outer surface of the second cylindrical section 86 to an inner surface thereof. At a proximal end 92 of the hub 30, the inner surface includes an annularly shaped principal recess 94 that forms a shoulder at a proximal end of the passageway 88. Additional semi-cylindrical recesses 96 are located around the circumference of the annularly shaped principal recess 94. A second annularly shaped recess 98 extends around the inner surface of the hub 30 in the area in which the semi-cylindrical recesses 96 are located, leaving individual flanges 100 extending radially inwardly along the inner surface at the proximal end 92 of the hub 30.

Figure 8:
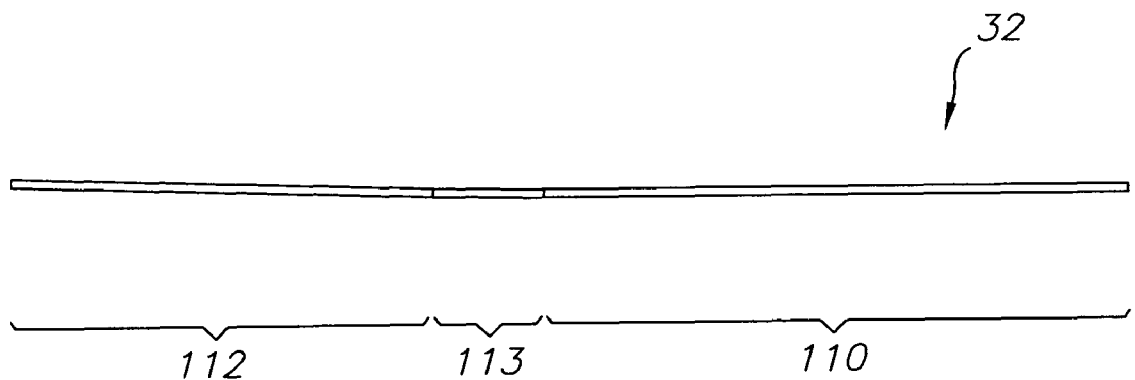
FIG. 8 is a side view of a guide tube having a passageway for slidably receiving a pull wire.

The guide tube 32, shown in FIG. 8, is tube shaped and has a passageway extending longitudinally therethrough. A proximal section 110 and a distal section 112 are both straight and form an angled relation to each other. A transition section 113 is curved and connects the proximal and distal sections 110, 112.

The component parts of the handle 22 are preferably assembled as shown in FIG. 2. A first thrust washer 114 is placed on the outer surface of the first core member 26 distally adjacent the flange 34 (see FIG. 3A) of the first core member 26, and the first core member 26 is inserted into the rotator handle 28 through the proximal end 62 (see FIG. 5A) of the rotator handle 28. A second thrust washer 116 is placed proximal to the proximal end 36 of the first core member 26. The first thrust washer 114 is sandwiched between the annular flange 72 of the rotator handle 28 and the flange 34 of the first core member 26. The flange 34 sits in the area between the annularly shaped flange 72 and the second annularly shaped recess 74 of the rotator handle 28. A snap ring 118 is placed in the second annularly shaped recess 74 (see FIG. 5B) and contacts the second thrust washer 116, thus retaining the position of the first core member 26.

A first core member fastener (not shown) engages the first fastener opening 44 (see FIG. 3B) of the first core member 26. A ball bearing 122 is placed in the first fastener opening 44. The access opening 76 (see FIG. 5B) of the rotator handle 28 allows for access to the first core member fastener.

The partially threaded member 27 is screwed into the rotator handle 28 from the distal end 63 of the rotator handle 28. The exterior thread 54 of the partially threaded member 27 engages the threaded portion 68 of inner surface of the rotator handle 28. The first core member 26 sits inside the passageway 52 of the partially threaded member 27. When the partially threaded member 27 is fully engaged within the rotator handle 28 as shown in FIG. 2, the proximal end 48 of the partially threaded member 27 abuts the annularly shaped flange 72 of the rotator handle 28.

A dowel 124 engages the dowel opening 56 of the partially threaded member 27 (see FIG. 4B) and extends from the outer surface of the partially threaded member 27 into the first slot opening 38 of the first core member 26. When the partially threaded member 27 is fully engaged in the rotator handle 28, the dowel 124 is located in the area of the passageway 64 of the rotator handle 28 corresponding to the first annularly shaped recess 70 (see FIG. 5B). The dowel 124 is placed into the dowel opening 56 of the partially threaded member 27 through the second access opening 77 of the rotator handle 28 as the partially threaded member 27 is screwed into the rotator handle 28 and the dowel opening 56, second access opening 77, and first slot opening 38 of the first core member 26 are aligned.

The end cap 23 is secured to the proximal end 62 of the rotator handle 28. The end cap 23 includes a cylindrically shaped first contact surface 126 which contacts the inner surface of the rotator handle 28 and a second contact surface 128 which contacts the proximal end 62 of the rotator handle 28. A passageway 130 extends through the end cap 23 and is placed in communication with the passageway 64 of the rotator handle 28. The first contact surface 126 of the end cap 23 is aligned with the fastener openings 75 of the rotator handle 28. Set screws (not shown) engage the fastener openings 75 to secure the end cap 23 to the rotator handle 28.

The second core member 29 is placed in the passageway 88 of the hub 30. The slot opening 84 (see FIG. 6B) of the second core member 29 is aligned with the hemostasis valve opening 90 (see FIG. 7B) of the hub 30. A slab 134 is placed in the annularly shaped principal recess 94 of the hub 30 proximally adjacent to the second core member 29. The slab 134 is preferably formed of polyisoprene, and includes a central opening 136 placed in communication with the passageway 88 of the second core member 29 as well as a guide tube opening 138 which is placed in communication with the slot 82 of the second core member 29. The slab 126 can be adhered to the inner surface of the hub 30.

The proximal section 110 (see FIG. 8) of the guide tube 32 is inserted into the slot 40 of the first core member 26. The guide tube 32 passes through the slab 134. The distal section 112 of the guide tube 32 is inserted into the slot 82 of the second core member 29.

The pointed annular tip 61 (see FIG. 4B) of the partially threaded member 27 is pressed into the slab 134, and the individual flanges 100 (see FIG. 7A) at the proximal end 92 of the hub 30 engage in the annularly shaped groove 58 of the partially threaded member 27 to connect the hub 30 to the partially threaded member 27. The flanges 100 ride along the tapered surface 60 of the partially threaded member 27 before engaging the annularly shaped groove 58 of the partially threaded member 27. Upon assembly between the partially threaded member 27 and the hub 30, and when the partially threaded member 27 is fully engaged in the rotator handle 28, the proximal end 92 of the hub 30 abuts the rotator handle 28. Further, as shown in FIG. 2, the center section 113 of the guide tube 32 passes through the slab 134.

Figure 9:
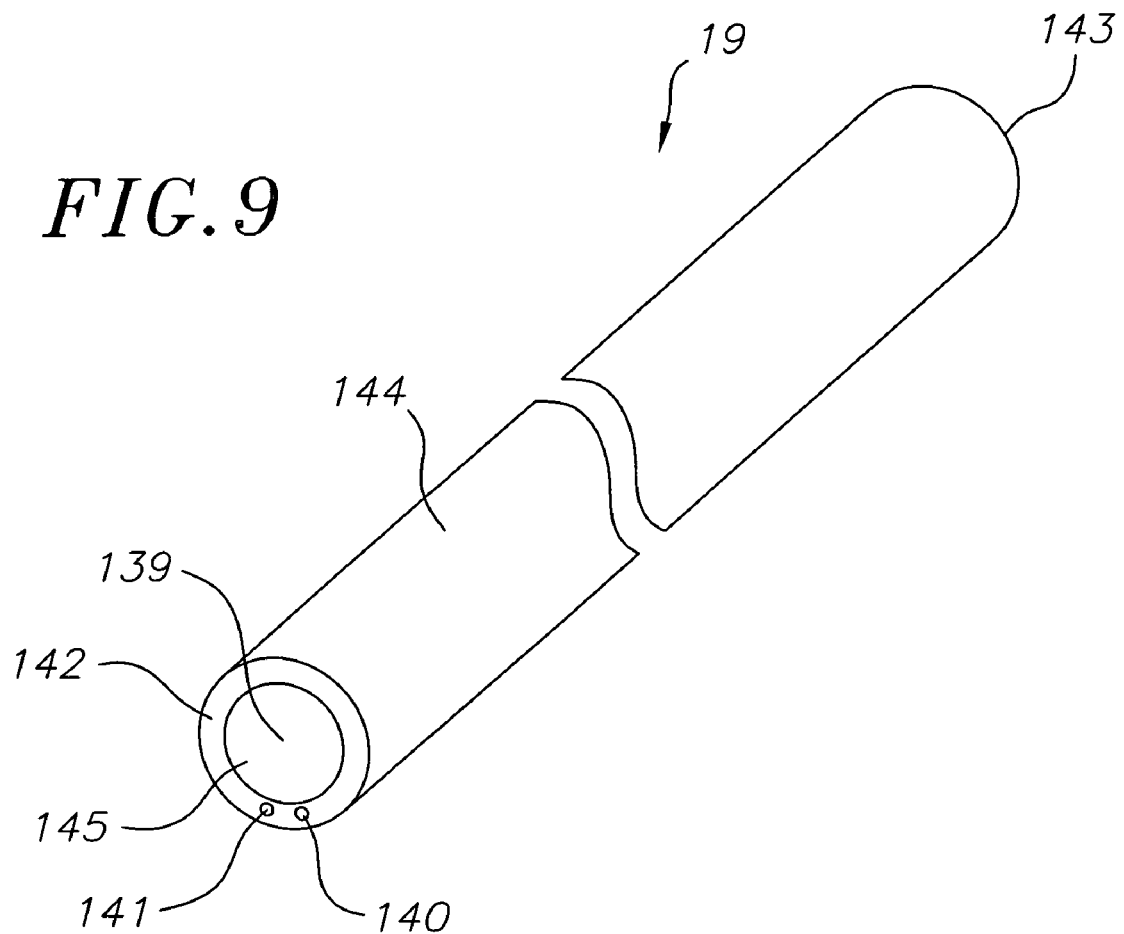
FIG. 9 is a perspective view of a sleeve formed with a central lumen.

With reference to FIG. 9, the sleeve 19 is preferably an elongate tubular structure formed with a center lumen 139 and first and second outer lumens 140, 141. The sleeve includes a proximal end 142 and a distal end 143, an outer surface 144, and an inner surface 145. The sleeve 20 may be formed from any suitable material, but preferably is made of thermoplastic elastomers formed from polyether block amides, commercially available as Pebax®. Toward the distal end 143, the sleeve 19 includes a soft durometer section capable of flexing. The soft durometer section of the sleeve 19 is preferably made of 55D Pebax®, and is capable of flexing, as described below. A remaining portion of the sleeve 19 is preferably made of 72D Pebax®, which is more stiff than 55D Pebax®. The stiffness of 72D Pebax prevents the sleeve from excessive bending, thus giving the operator the ability to push the delivery system 10 through the potentially constricting body vessel, and allowing the delivery system 10 to more effectively track to the native valve site, as described below. The sleeve 19 can also be formed of wire braid anywhere along the length thereof. Wire braid can also contribute to the stiffness and pushability of the delivery system 10.

Figure 10:
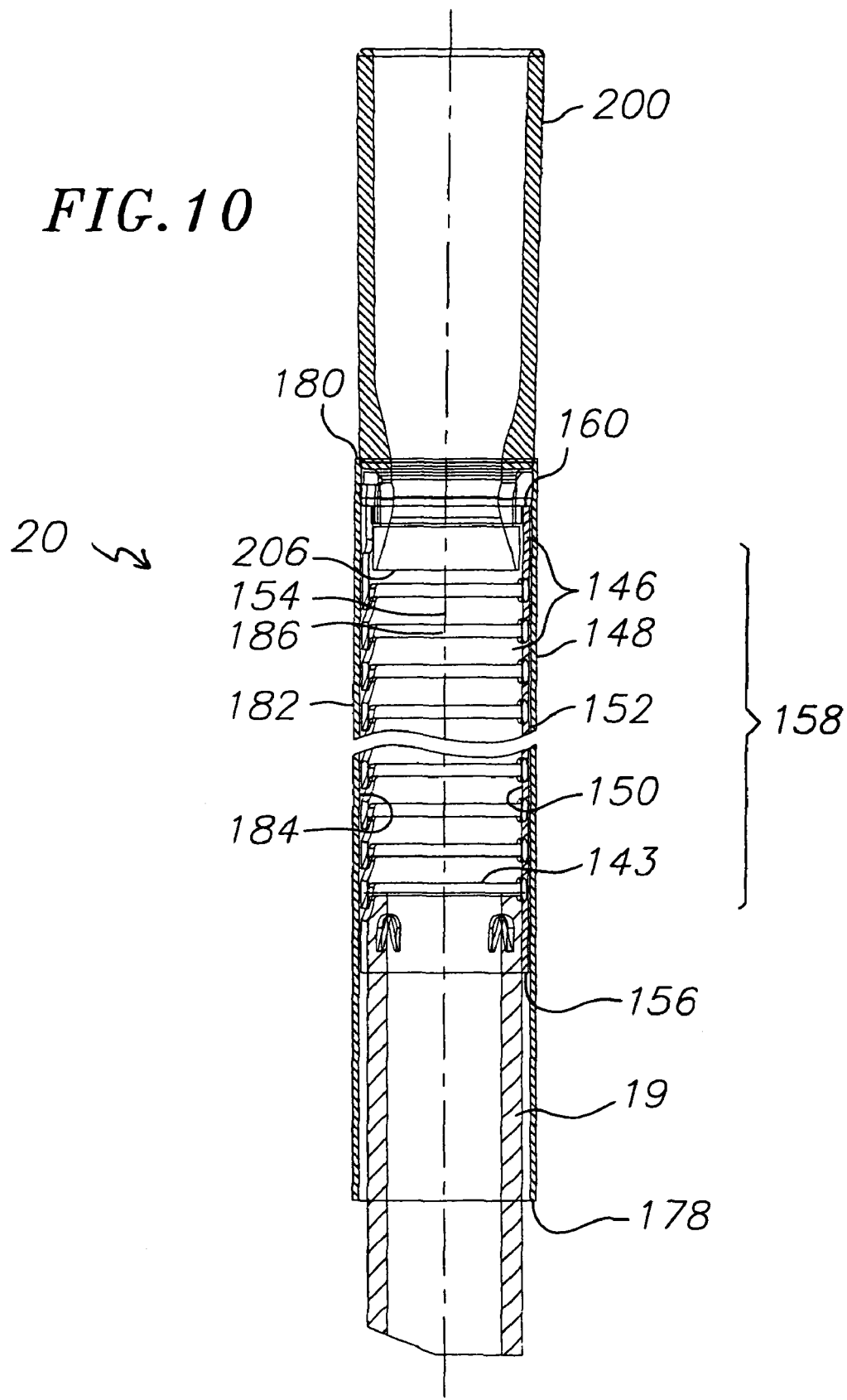
FIG. 10 is a cross sectional view of a distal portion of a delivery sleeve assembly.
Figure 11:
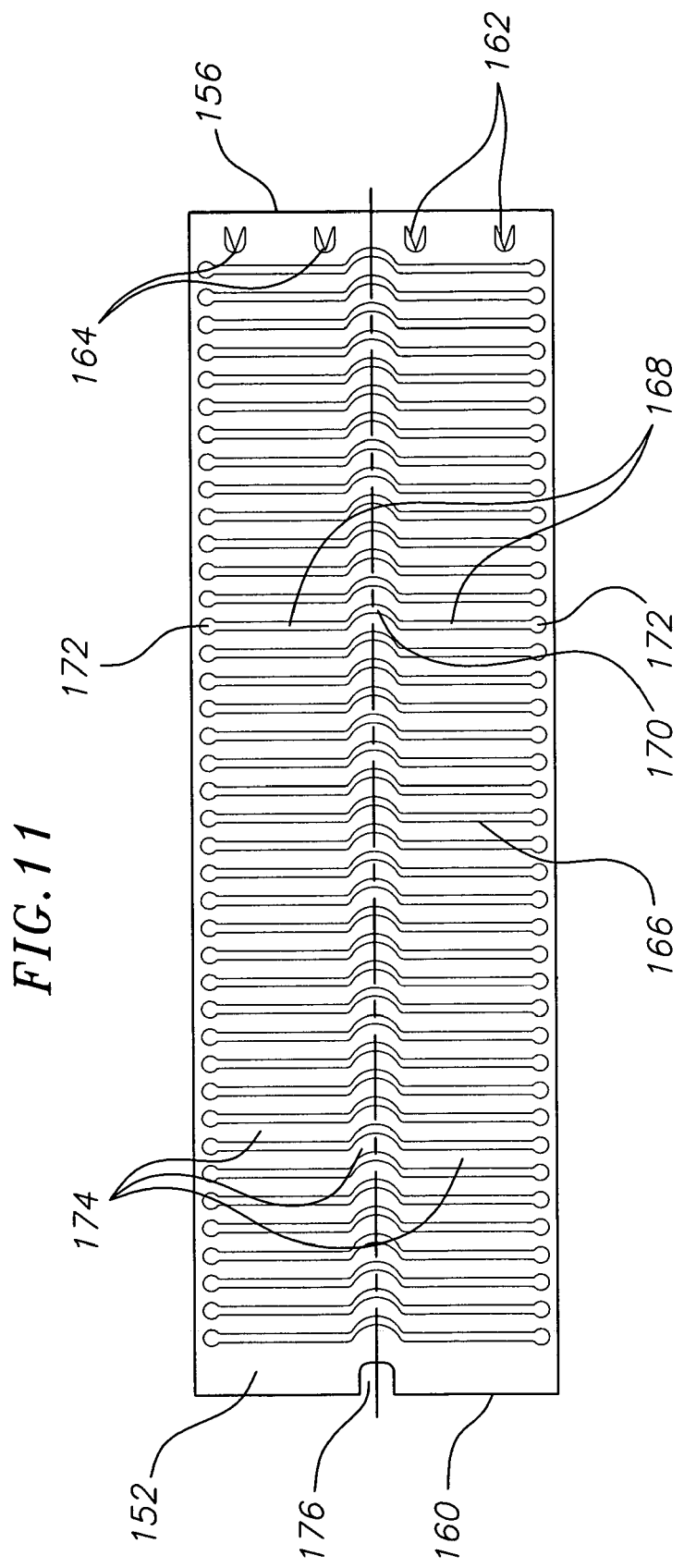
FIG. 11 is a side view of a flex tube which provides a steerable section, wherein the flex tube has been laid flat for purposes of illustration.

With reference to FIG. 10, the steerable section 20 of the delivery sleeve assembly is shown in cross section. The steerable section generally includes a flex tube 146 and a cover 148. The flex tube 146 is preferably tube shaped, having an inner surface 150, an outer surface 152, and a passageway 154 extending therethrough. The flex tube 146 is further defined by a proximal end 156, a center section 158, and a distal end 160. With reference to FIG. 11, a plurality of v-shaped notches 162 are provided, such as by laser cutting, in the flex tube 146 adjacent the proximal end 156. The notches 162 are shaped to provide pointed barbs 164. Along the center section 158 of the flex tube 146, circumferentially extending elongate openings 166 are provided. Each elongate opening 166 preferably includes two elongate portions 168 connected by a curved portion 170. Circular portions 172 are provided at the ends of the elongate openings. Tube portions 174 remain substantially intact and will be described in more detail below. A notch 176 is formed at the distal end 160 of the flex tube 146. In one preferred embodiment, the flex tube 146 is made of a stainless steel hypo-tube.

With reference again to FIG. 10, the cover 148 is preferably tube-shaped, having proximal and distal ends 178, 180, and including an outer surface 182 and an inner surface 184, with a passageway 186 extending longitudinally therethrough. In a preferred embodiment, the cover 148 is formed of soft durometer material such as 55D Pebax®. The soft durometer 55D Pebax® of the cover 148 allows it to stretch and flex, as described below.

The steerable section 20 is assembled by placing the flex tube 146 inside the cover 148. The cover 148 may be stretched prior to assembly to give the steerable section 20 desirable features, as outlined below. The outer surface of the flex tube 146 contacts the inner surface of the cover 148. The proximal end 178 of the cover 148 extends proximally from the proximal end 156 of the flex tube 146, and the distal end 180 of the cover 148 extends distally from the distal end 160 of the flex tube 146.

Figure 12:
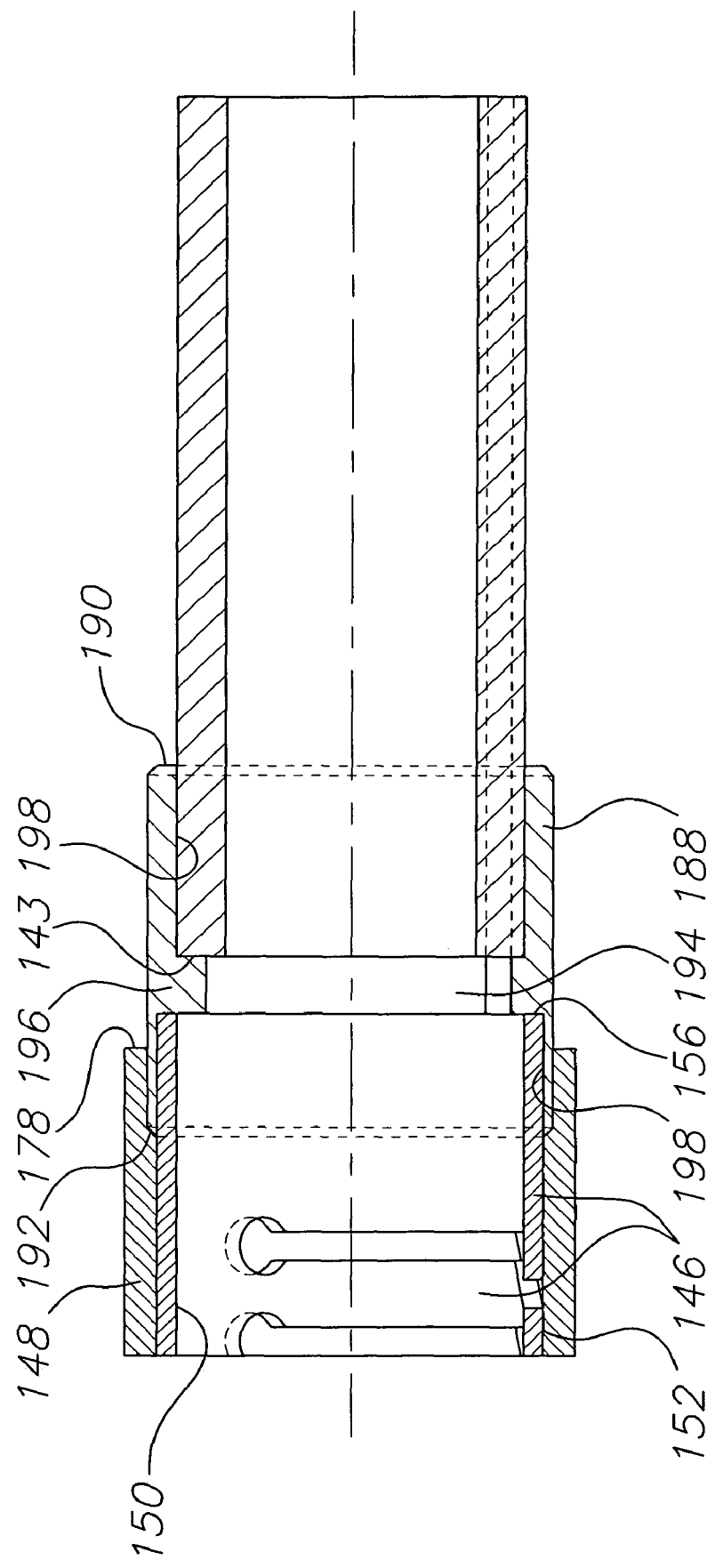
FIG. 12 is a cross sectional view of a portion of a delivery sleeve assembly according to an alternative embodiment.

With reference to FIG. 12, an alternative embodiment of the steerable section 20 includes a connector 188 having a proximal end 190 and a distal end 192. The connector 188 is tube shaped, having a passageway 194 longitudinally extending therethrough. An annularly shaped flange 196 protrudes from an inner surface 198 of the connector 188.

To assemble the alternative embodiment of the steerable section 20 including the connector 188, the proximal end 156 of the flex tube 146 is inserted into the passageway 194 of the connector 188 until it abuts the annularly shaped flange 196. The outer surface 152 of the flex tube 146 contacts the inner surface 198 of the connector 188, and can be adhered thereto using adhesion. The cover 148 is placed over the flex tube 146 and the connector 188. The proximal end 190 of the connector 188 extends proximally from the proximal end 178 of the cover 148, and the distal end 180 of the cover 148 extends distally from the distal end 160 of the flex tube 146 (see FIG. 10).

Figure 13:
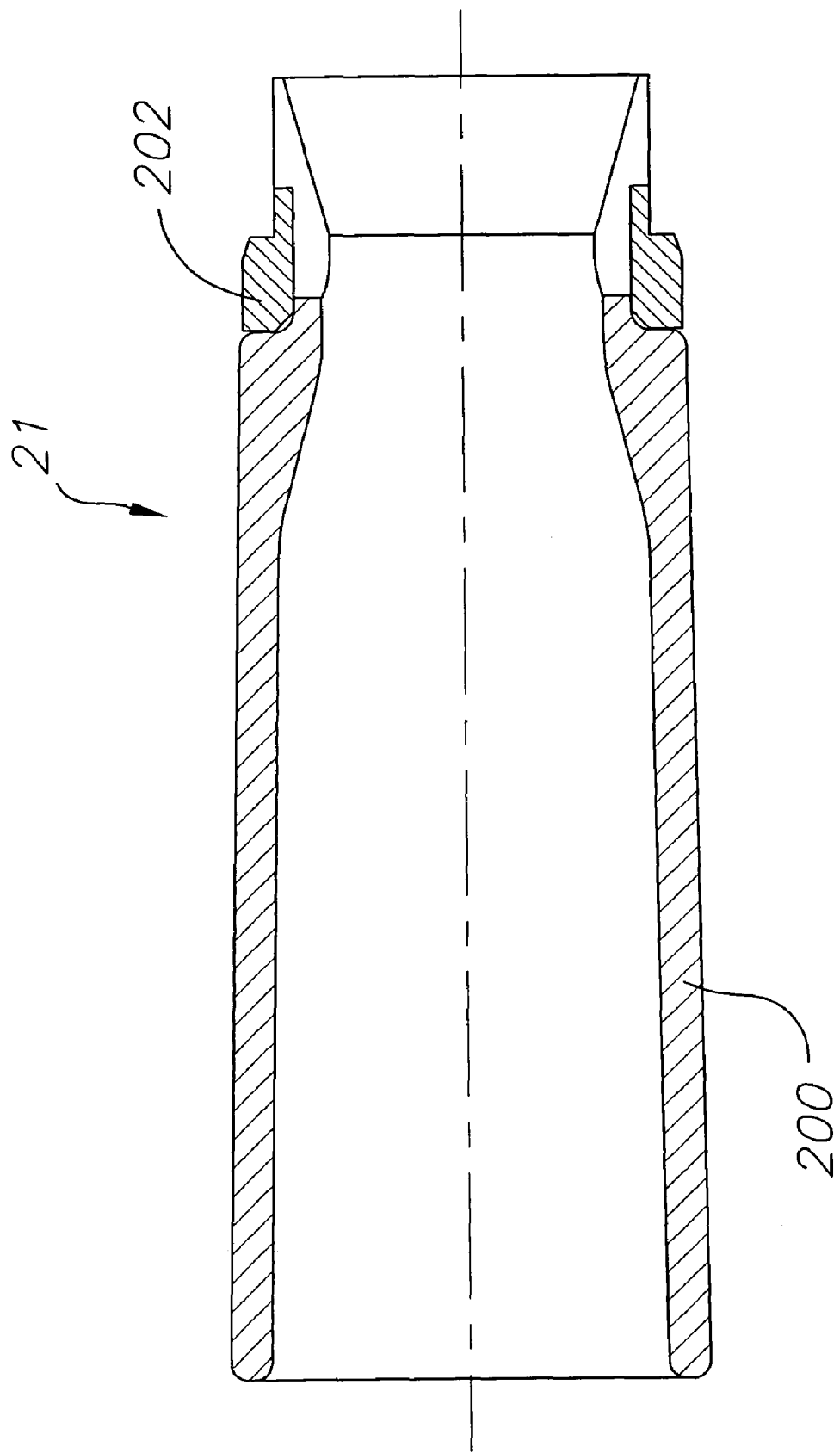
FIG. 13 is a cross sectional view of a shroud section of the delivery sleeve assembly.
Figure 14A:
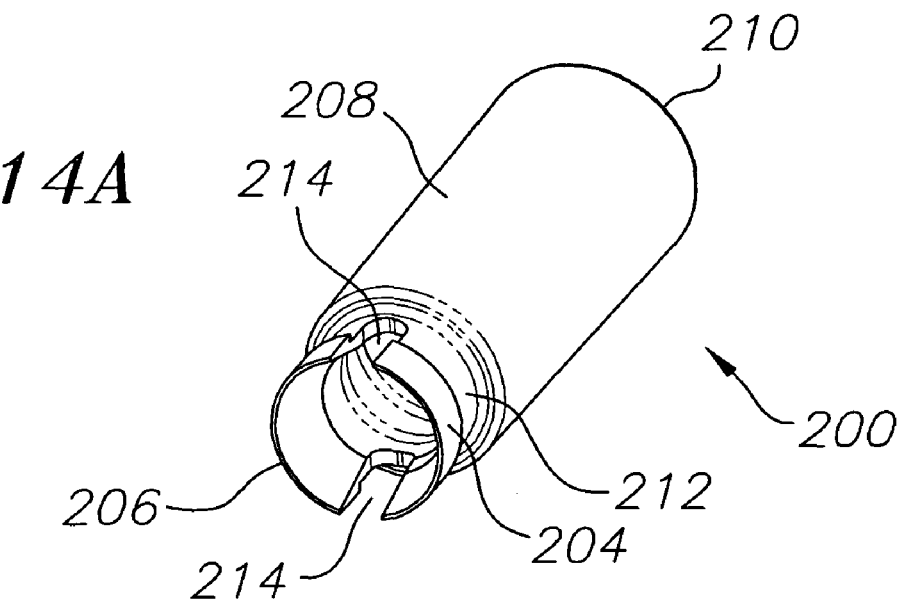
FIGS. 14A and 14B are perspective and cross sectional views, respectively, of a shroud which forms a portion of the shroud section of FIG. 13.
Figure 14B:
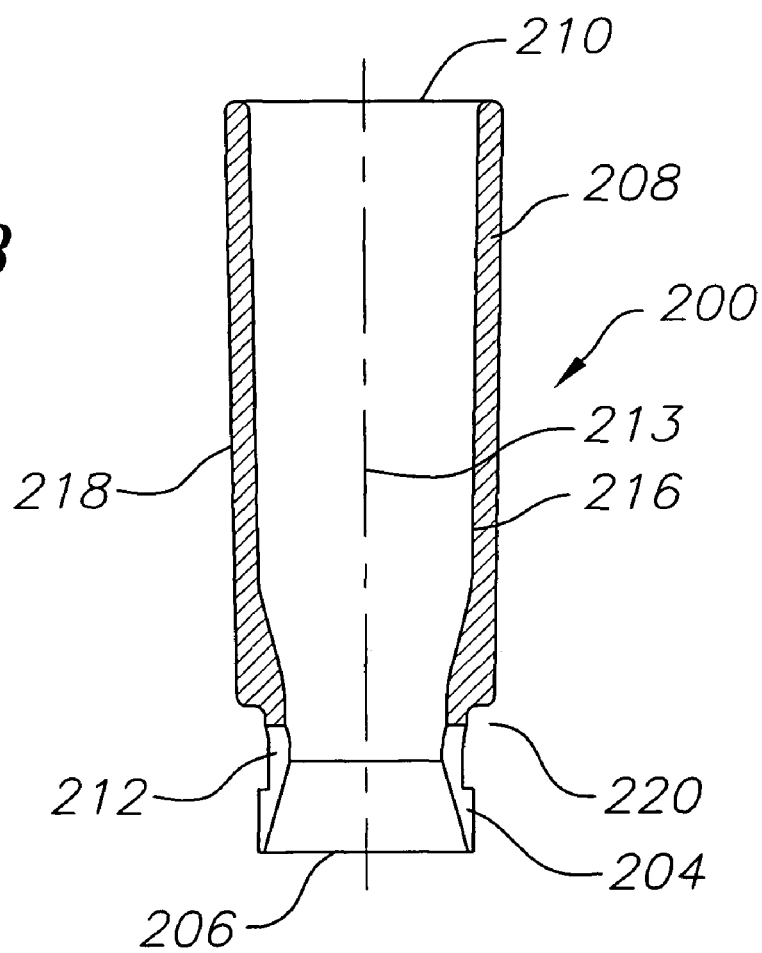

With reference to FIG. 13, the shroud section 21 is shown in cross-section. The shroud section 21 generally includes a shroud 200 and a ring 202. With reference to FIGS. 14A and 14B, the shroud 200 is preferably cylindrical-shaped and comprises three continuous cylindrical sections: a rim 204 near a proximal end 206, a main body 208 near a distal end 210, and a neck 212 located therebetween. A passageway 213 extends through the shroud 200, which includes an inner surface 216 and an outer surface 218. Slots 214 run from the proximal end 210 of the shroud 200 into the neck 212. The neck 212 has a smaller circumference than the rim 204 and the main body 208, resulting in a groove 220 along the outer surface 218 of the shroud 200.

Figure 15A:
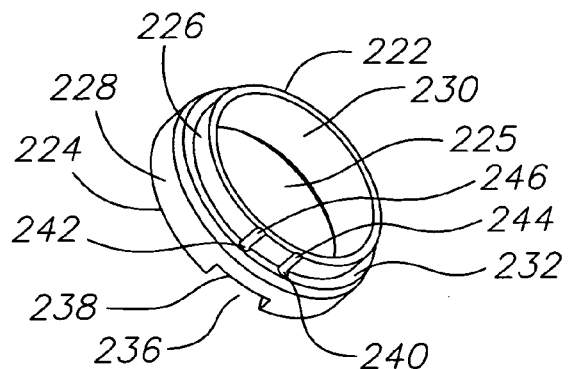
FIGS. 15A, 15B, and 15C are perspective, cross sectional, and bottom views, respectively, of a ring which forms a portion of the shroud section of FIG. 13.
Figure 15B:
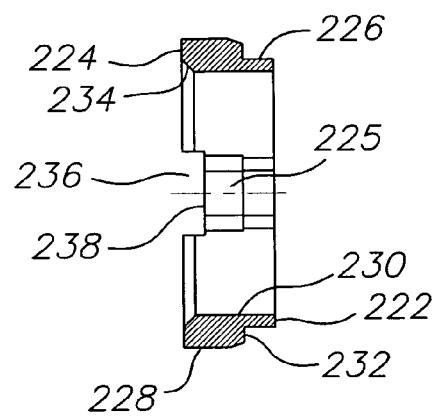
Figure 15C:
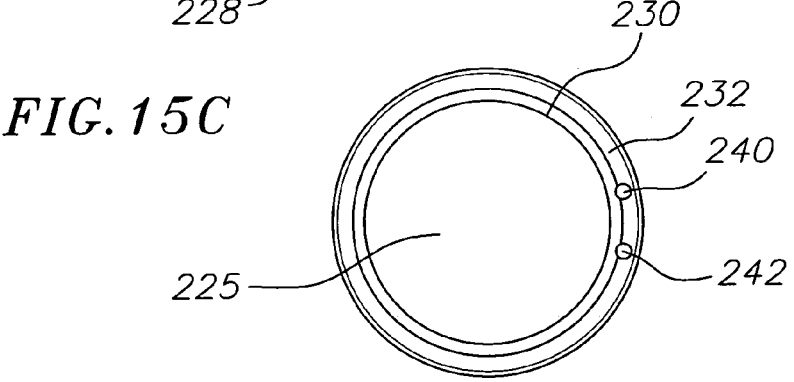

With reference now to FIGS. 15A through 15C, the ring 202 has a proximal end 222, a distal end 224 and a passageway 225 extending longitudinally therethrough. The ring 202 includes a proximal outer surface 226, a distal outer surface 228, and an inner surface 230. An outer face 232 runs perpendicular to the proximal and distal outer surfaces 226, 228 of the ring 202 and connects the proximal and distal outer surfaces 226, 228, which generally run parallel to one another. The inner surface 230 includes an angled surface 234 toward the distal end 224, causing the passageway 225 of the ring to increase in diameter near the distal end 224 of the ring 202.

A slot 236 extends into the distal end of the ring 202 and through the distal outer surface 228 to the inner surface 230 and parallel to a central axis of the ring 202, creating a slot face 238 opposed to the outer face 232. A first lumen 240 and a second lumen 242 extend from the slot face 238 to the outer face 232 of the ring 202. The proximal outer surface 226 also includes a first semi-cylindrical recess 244 and a second semi-cylindrical recess 246 which run parallel to the central axis of the ring 202 and pass from the proximal end 222 to the outer face 232 of the ring 202. The first cylindrical recess 244 is aligned with the first lumen 240, and the second cylindrical recess 246 is aligned with the second lumen 242.

The shroud section 21 is formed by inserting the proximal end of the shroud 200 into the ring 202 according to FIG. 13. The rim 204 flexes to permit this. The ring 202 fits snugly in the groove 220 (see FIG. 14B), such that the inner surface 230 and the proximal and distal ends 222, 224 of the ring 202 (see FIG. 15A) contact the outer surface 218 of the shroud 200. The ring 202 is situated so that either of the slots 214 of the shroud 200 (see FIG. 14A) is aligned with the slot 236 of the ring 202.

Figure 16:
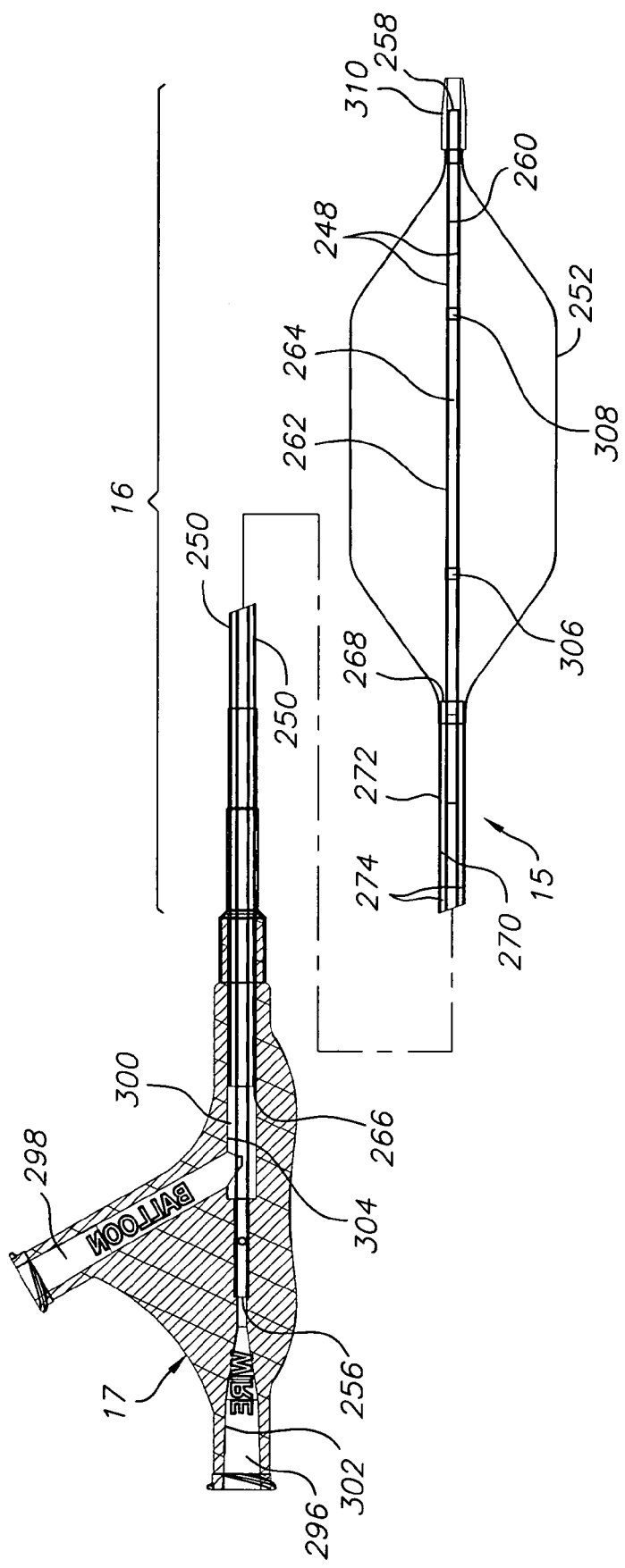
FIG. 16 is a cross sectional view of a balloon catheter configured for use with the heart valve delivery system.

With reference to FIG. 16, the balloon catheter 15 includes a tube section 16 and a support 17. The tube section 16 includes a guidewire shaft 248, a balloon shaft 250, both of which are connected to the support 17, and a balloon 252. The guidewire shaft 248 having a proximal end 256 and a distal end 258 includes an inner surface 260, an outer surface 262, and a passageway 264 longitudinally extending therethrough. The guidewire shaft 248 can be formed of nylon, braided stainless steel wires, or Pebax® at differing portions along its length, according to the need for rigidity and flexibility. Teflon® can be used to form the inner surface 260 of the guidewire shaft 248. The balloon shaft 250 having a proximal end 266 and a distal end 268 includes an inner surface 270, an outer surface 272, and a passageway 274 longitudinally extending therethrough. The balloon shaft 250 can be formed of any combination of nylon, Pebax®, or braided stainless steel wires at differing portions along its length, according to the need for rigidity and flexibility.

With reference now to FIGS. 17A and 17B, the balloon 252 has a proximal end 276 and a distal end 278 includes an inner surface 280, an outer surface 282, and a passageway 284 extending longitudinally therethrough. When viewed from the proximal end 276 to the distal end 278, the balloon 252 includes five portions: a first slender portion 286, a first cone portion 288, a main cylindrical portion 290, a second cone portion 292, and a second slender portion 294. The balloon 252 can be formed of nylon, and is rated at a burst pressure of 6-8 atm. In preferred embodiments, the expanded diameter of the balloon ranges from about 20 to 28 mm and, more preferably, is about 23 mm.

With reference again to FIG. 16, the support 17 includes a wire inlet opening 296, an fluid inlet opening 298, and a main shaft opening 300. The wire inlet opening 296 includes an interior surface 302, and the main shaft opening 300 likewise includes an interior surface 304. The openings 296, 298, 300 are arranged so as to be in communication with one another.

The balloon catheter 15 is assembled as shown in FIG. 16. The guidewire shaft 248 is inserted into the main shaft opening 300. The proximal end of the guidewire shaft 248 is placed in the wire inlet opening 296, and the outer surface 262 of the guidewire shaft 248 is secured to the interior surface 302 of the wire inlet opening 296, for example, by adhesion. The guidewire shaft 248 is of a smaller diameter than the main shaft opening 300 and as such, does not contact the interior surface 304 of the main shaft opening 300.

The balloon shaft 250 is placed over the guidewire shaft 248. The proximal end 266 of the balloon shaft 250 is placed in the main shaft opening 300 of the support 17, and the outer surface 272 of the balloon shaft 250 is secured to the interior surface 304 of the main shaft opening 300. As shown in FIG. 16, the guidewire shaft 248 is of a smaller diameter than the balloon shaft 250, and the outer surface 262 of the guidewire shaft 248 does not contact the inner surface 270 of the balloon shaft 250 to permit air flow.

The proximal end 256 of the guidewire shaft 248 extends proximally from the proximal end 266 of the balloon shaft 250, and the distal end 258 of the guidewire shaft extends distally from the distal end 268 of the balloon shaft 250.

The proximal end 276 of the balloon 252 is placed over the distal end 268 of the balloon shaft 250. The inner surface 280 of the balloon 252 in the area of the first slender portion 286 is secured to the outer surface 272 of the balloon shaft 250. The distal end 278 of the balloon 252 is placed over the distal end 258 of the guidewire shaft 248. The inner surface 280 of the balloon 252 in the area of the second slender portion 294 is secured to the outer surface 262 of the guidewire shaft 248. The balloon 252 can secured to the balloon shaft 250 and the guidewire shaft 248 by a process involving the curing of adhesive with ultraviolet light or laser welding.

First and second marker bands 306, 308 are placed along the guidewire shaft 248 within the passageway 284 of the balloon 252. The marker bands 306, 308 can be secured to the outer surface 262 of the guidewire shaft 248 by an adhesive or swaging. The position of the first marker band 306 roughly corresponds to the transition between the first cone portion 288 and the main cylindrical portion 290 of the balloon 252 (see FIG. 17B). The position of the second marker band 308 roughly corresponds to the transition between the main cylindrical portion 290 and the second cone portion 292 of the balloon 252 (see FIG. 17B). The marker bands 306, 308 can be formed of 90 percent platinum and 10 percent iridium in order to indicate by fluoroscopy, a process known in the art, the position of the balloon catheter 19 within the patient. A soft tip 310 located distally from the balloon 252 is placed over the distal end 258 of the guidewire shaft 248.

The delivery sleeve assembly 18 is formed by joining the sleeve 19 and steerable section 20. The distal end 143 of the sleeve 19 is inserted into the passageway 186 of the cover 148 and the passageway 154 of the flex tube 146 as shown in FIG. 10. The sleeve 19 is positioned relative to the steerable section 16 such that the first and second outer lumens 140, 141 are aligned with the curved portions 170 of the elongate openings 166 of the flex tube 146. The outer surface 144 of the sleeve 19 is secured to the inner surface 150 of the flex tube 146, for example, by thermal or adhesive joining. Further, the barbs 164 may engage the distal end 143 of the sleeve 19 to make the connection. The inner surface 184 of the cover 148 is also secured to the outer surface 144 of the sleeve 19 at the proximal end 178 of the cover 148 by adhesive or by thermal joining.

In the alternative embodiment (see FIG. 12) involving the connector 188, the outer surface 144 of the sleeve 19 is secured at its distal end 143 to the inner surface 198 of the connector 188 toward the proximal end 190 of the connector 188. The distal end 143 of the sleeve 19 abuts the annularly shaped flange 196 of the connector 188.

The shroud section 21 is also joined to the steerable section 20 to form the delivery sleeve assembly 18 (see FIG. 10). The proximal end 206 of the shroud 200 is inserted into the passageway 186 of the cover 148 at the distal end 180 of the cover 148. The proximal end 206 of the shroud 200 is further inserted into the passageway 154 of the flex tube 146 at the distal end 160 of the flex tube 146. The slot 214 of the shroud 200 is aligned with the notch 176 of the flex tube 146 (see also FIGS. 11 and 14A).

The outer surface 218 of the shroud 200 in the area of the rim 204 is secured to the inner surface 150 of the flex tube 146. The proximal outer surface 226 of the ring 202 is secured to the inner surface 150 of the flex tube 146 adjacent the distal end 160 of the flex tube 146. The distal end 160 of the flex tube 146 abuts the outer face 232 of the ring 202. The shroud section 21 can be secured to the flex tube 146 with mechanical bond and adhesive.

The inner surface 184 of the cover 148 is secured to the distal outer surface 228 of the ring 202. The inner surface 184 of the cover 148 is also secured to the outer surface 218 of the shroud 200 in the area of the main body 208. These connections can be made by adhesive or thermal joining, or both. The main body 208 of the shroud 200 extends distally from the distal end 180 of the cover 148.

The delivery sleeve assembly 18 is connected to the handle 22 as the proximal end 142 of the sleeve 19 is inserted into the passageway 88 of the hub 30 and the outer surface 144 of the sleeve 19 is secured to the inner surface of the hub 30, for example, by an adhesive.

A pull wire 312 shown in FIG. 2 is inserted into the delivery system 10. A first end of the pull wire 312 is placed in the first fastener opening 44 of the first core member 26. The first core member fastener (not shown) bears upon ball bearing 122, which secures the pull wire 312 in the first fastener opening 44. The pull wire 312 passes through the longitudinally extending access opening 46 (see FIG. 3B) of the first core member 26. The pull wire 312 passes through the passageway of the guide tube 32 which is located in the slot 40 of the first core member 26, the guide tube opening 138 of the slab 134, and the slot 82 of the second core member 29, and then through the passageway 88 of the hub 30. The pull wire 312 then passes through the first lumen 140 of the sleeve 19 (see FIG. 9). The pull wire 312 exits the sleeve 19 and passes through the passageway 154 of the flex tube 146 (see FIG. 10). The pull wire 312 passes through the first semi-cylindrical recess 244 and the first lumen 240 of the ring 202. The pull wire 312 is strung against the slot face 238 of the ring 202. The pull wire 312 is then returned through the second lumen 242 and the second semi-cylindrical recess 246 of the ring 202. The pull wire 312 passes again through the passageway 154 of the flex tube 146. The pull wire 312 passes through the second outer lumen 141 of the delivery sleeve 19, through the passageway 88 of the hub 30 (again), through the passageway of the guide tube 32 (again), and through the access opening 46 of the slot 40 of the first core member 26. A second end of the pull wire 312 is secured to the first core member 26 by pressure exerted by the first core member fastener (not shown) on the ball bearing 122, which secures the pull wire 312. The pull wire 312 can be formed of nitinol or stainless steel.

With reference now to FIGS. 1 and 16, a preferred method of using the heart valve delivery system 10 will now be described in more detail. The devices and methods disclosed herein are particularly well-suited for replacing a stenotic aortic valve. Those skilled in the art will recognize that it may be necessary to pre-dilate the leaflets of the stenotic aortic valve before deploying a prosthetic valve within the aortic valve. Pre-dilation increases the flow area through the aortic valve and creates an opening in the leaflets of sufficient size to receive the prosthetic valve. Pre-dilatation is preferably achieved using an expandable member, such as a dilatation balloon catheter. Additional details regarding pre-dilatation and valve replacement can be found in Applicant's co-pending application Ser. No. 10/139,741, filed May 2, 2002.

The assembly and operation of the heart valve delivery system 10 will now be described. During assembly, the balloon catheter 15 is inserted into the opening created by the assembly of the handle 22 and the delivery sleeve assembly 18. The support 17 of the balloon catheter 15 is located proximally to the handle 22. The balloon shaft 250, and the guidewire shaft 248, pass through the passageway 130 of the end cap 23 (see FIG. 2), the passageway 33 of the first core member 26, the central opening 136 of the slab 134, the passageway 78 of the second core member 29, the passageway 88 of the hub 30, the central lumen 139 of the sleeve 19, and the passageway 154 of the flex tube 146. The balloon shaft 250 passes into the passageway 213 of the shroud 200 according to FIG. 18A, while the guidewire shaft 248 passes through the passageway 213 of the shroud 200. The proximal end 276 of the balloon 252 is located in the passageway 213 of the shroud 200, and the balloon 252 extends distally from the distal end 210 of the shroud 200.

Figure 18A:
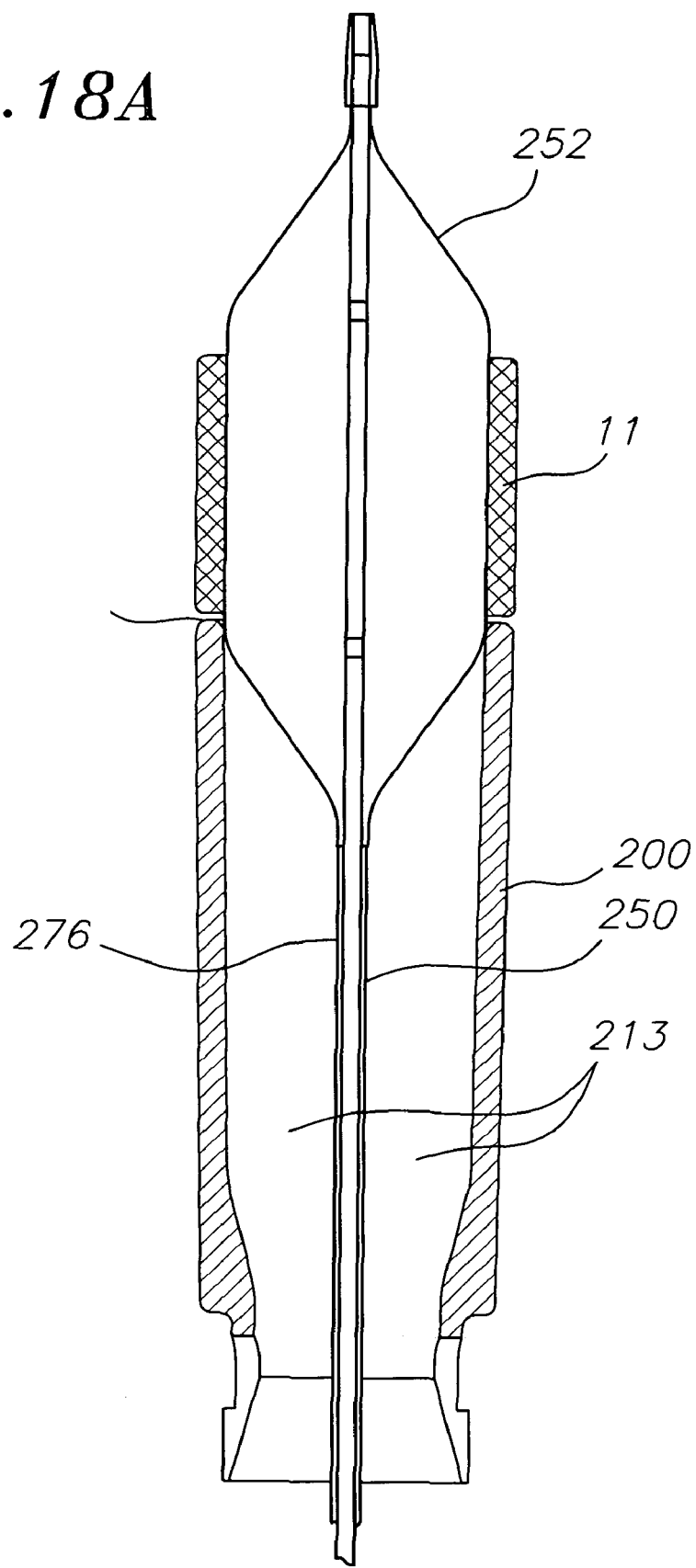
Figure 18B:
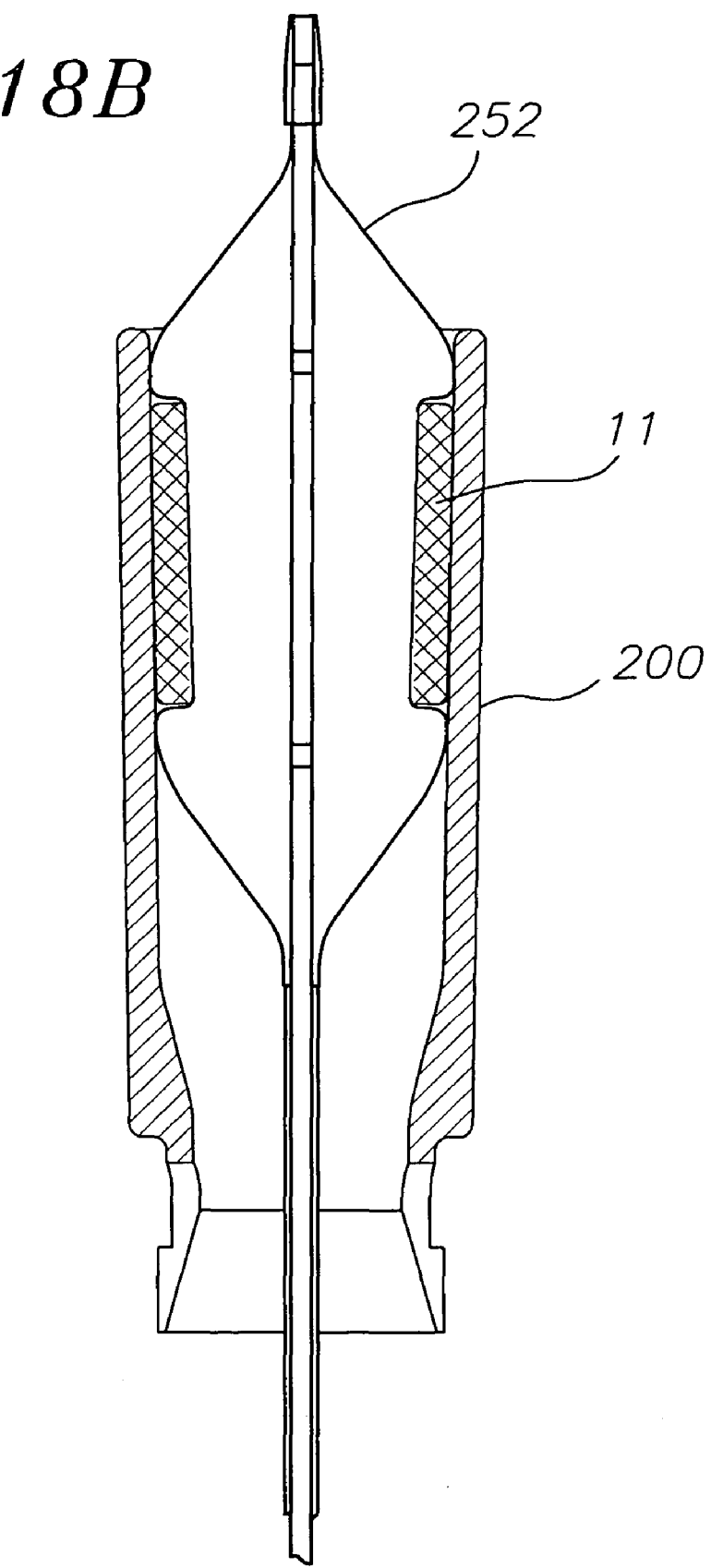

The prosthetic valve 11 is mounted onto the main cylindrical portion 290 of the balloon 252, distally from the distal end 210 of the shroud 200, as shown in FIG. 18A. The valve 11 is known in the art and is collapsible to a first position over the balloon 252, as shown in FIG. 1. Alternatively, the valve 11 can be mounted on the balloon 252 and placed inside the shroud 200, as shown in FIG. 18B.

The valve 11 can take a variety of different forms. In preferred embodiments, the valve generally comprises an expandable stent portion that supports a valve structure. The stent portion has sufficient radial strength to hold the valve at the treatment site and resist recoil of the stenotic valve leaflets. Additional details regarding preferred balloon expandable valve embodiments can be found in Applicant's U.S. Pat. Nos. 6,730,118 and 6,893,460, each entitled IMPLANTABLE PROSTHETIC VALVE, which are incorporated by reference herein. It will also be appreciated that the delivery system may be used with self-expanding prosthetic valves. For example, when using a self-expanding valve, a pusher may be substituted for the balloon catheter for ejecting the self-expanding valve from the delivery sleeve assembly.

With continued reference to the illustrated embodiment, the guide wire 14 is placed in the passageway 264 of the guidewire shaft 248 such that it extends distally from the distal end 258 of the guidewire shaft 248 and proximally from the wire inlet opening 296 of the support 17 of the balloon catheter 15. The process of inserting a catheter into the human body for tracking is known in the art, e.g. by U.S. Pat. No. 5,968,068 entitled ENDOVASCULAR DELIVERY SYSTEM, which is incorporated by reference herein.

Figure 19:
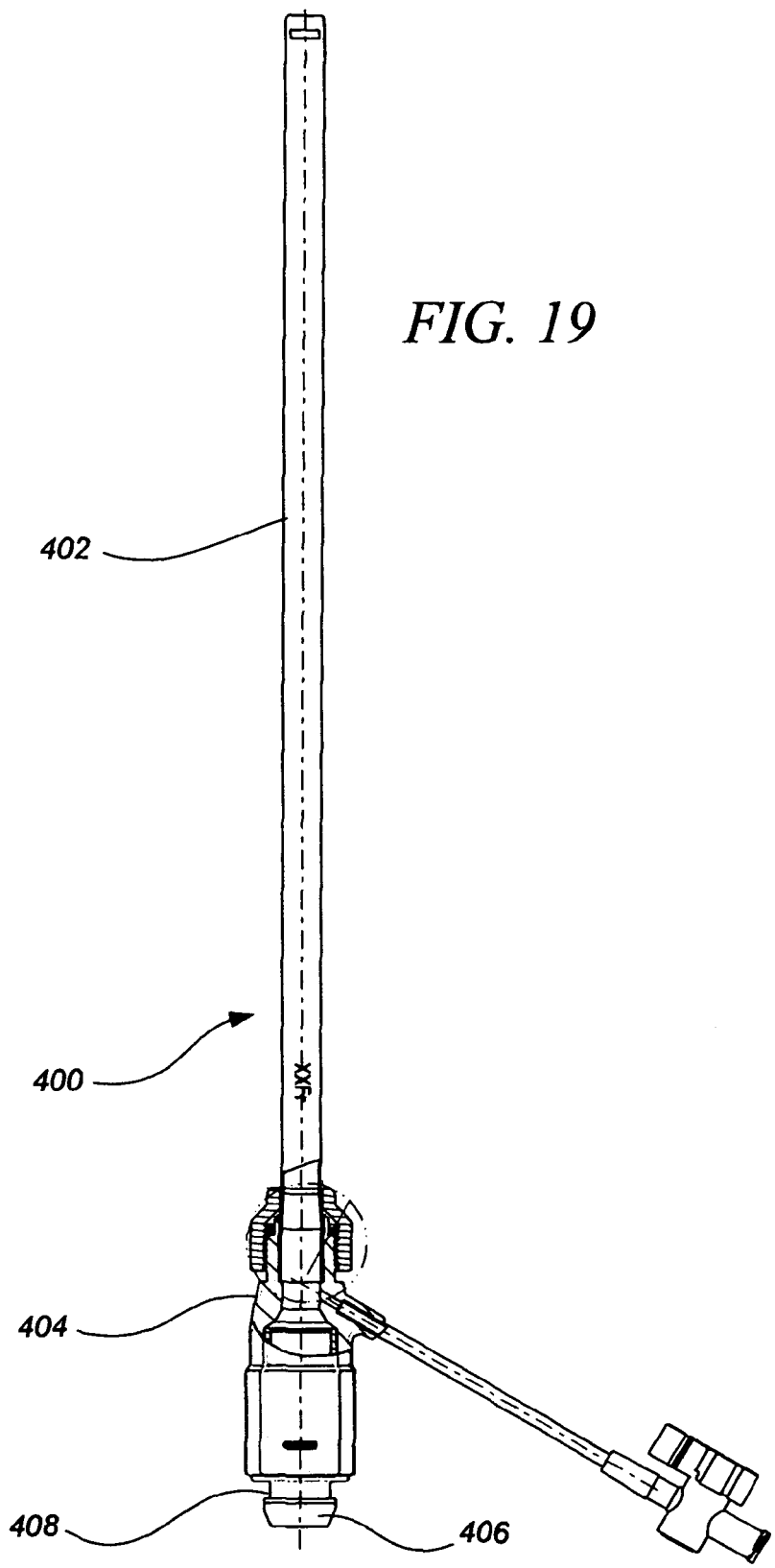
FIG. 19 is a side view of an introducer sheath assembly.

The guide wire 14 is placed in the body through a dilator (not shown) which expands the inner diameter of the body vessel in order to introduce an introducer sheath assembly 400, shown in FIG. 19, over the guide wire 14. Preferred dilator diameters range between 12 and 22 French. The introducer sheath assembly 400 includes an introducer sleeve 402 and an introducer housing 404 attached to a proximal end of the introducer sleeve 402. Introducer sheath assembly diameters of 22 or 24 French are preferred.

A series of valves are located inside the introducer housing 404. On a proximal end of the introducer housing 404, an end piece 406 is attached, the end piece having an opening extending into the introducer housing 404 in the area of the series of valves, and a ridge 408 facing a distal end of the introducer housing 404. The introducer sleeve 402 extends into the body vessel, with the introducer housing 404 located outside the body vessel on a proximal end on a proximal end of the introducer sleeve 402. In a preferred embodiment, the introducer sleeve 402 is coated with a hydrophilic coating and extends into the body vessel about 9 inches, just past the iliac bifurcation and into the abdominal aorta of the patient. The introducer sheath assembly 400 provides a mechanism for advancing the prosthetic valve into the aorta in a safe and effective manner.

With reference to FIG. 20, a loader assembly 500 includes a loader 502, a loader cap 504, and a loader seal 506. The loader 502 is tube shaped, having exterior threading 508 at a proximal end for connection with the loader cap 504. The loader 502 includes flexible flanges 510 extending parallel thereto and having snap ridges 512 facing the proximal end of the loader 502. The loader cap 504 includes a loader cap opening 514 in a proximal end thereof and a threaded inner surface 516 for engagement with the exterior threading 508 of the loader 502. The loader seal 506 is secured to the loader cap 504, and a loader seal opening 518 is aligned with the loader cap opening 514.

With reference to FIG. 21A, the loader cap 504 and loader seal 506 are passed onto the delivery system 10 as the sleeve 19 engages the loader cap opening 514 and loader seal opening 518. The distal end of the delivery system 10, passing over the guide wire 14, is inserted into the proximal end of the loader 502, as shown in FIG. 21B. The loader cap 504 screws onto the proximal end of the loader 502.

Figure 22:
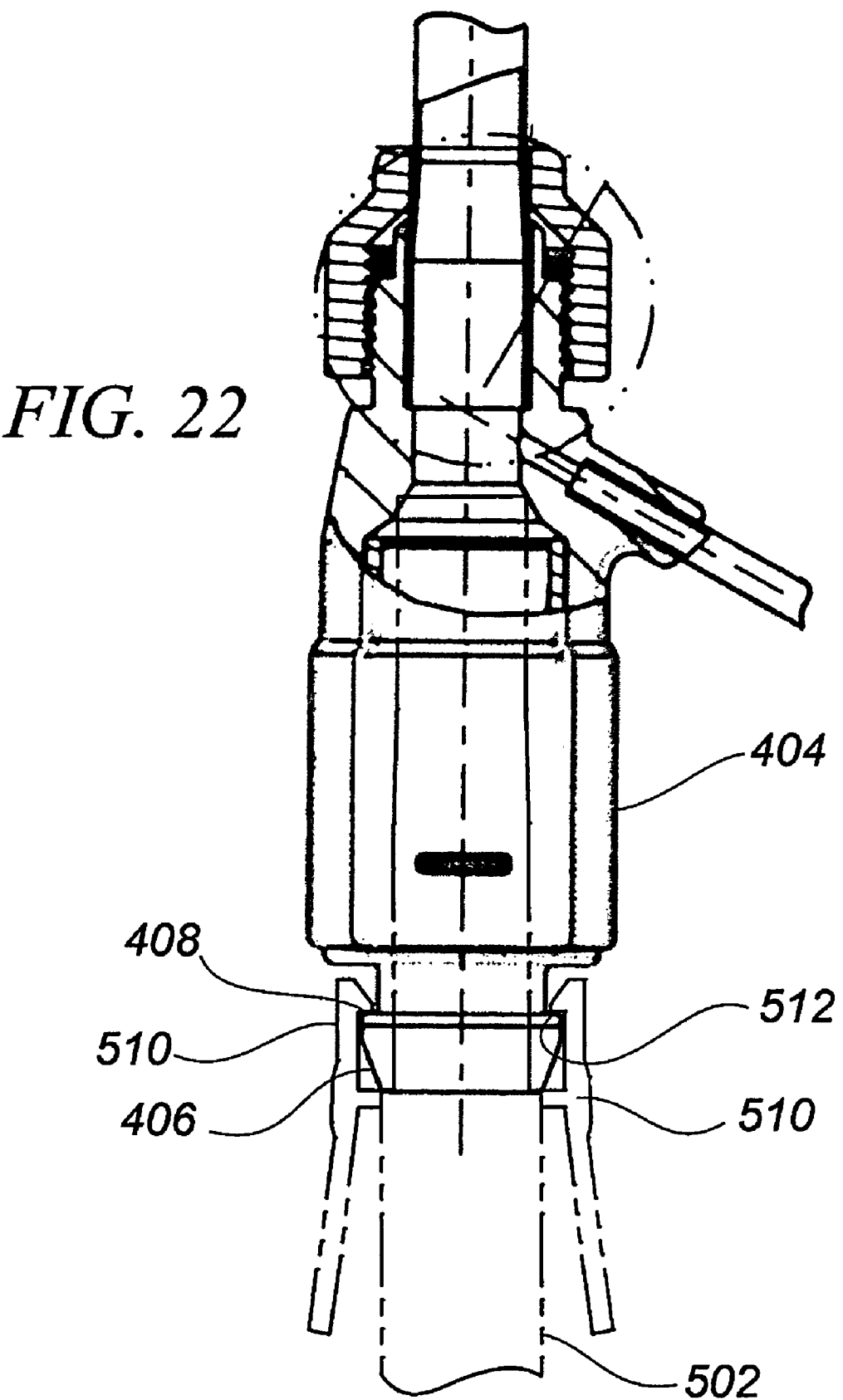
FIG. 22 is a side view illustrating the relationship between the delivery system, the introducer sheath assembly, and the loader assembly.

With reference to FIG. 22, the flexible flanges 510 of the loader 502 snap into the end piece 406 of the introducer housing 404. In this position, the ridge 408 of the end piece 406 bears against the snap ridge 512 of the flexible flanges 510, and the loader 502 passes through the series of valves located inside the introducer housing 404, thus placing the delivery system 10 in communication with an inner passageway of the introducer sheath and thus, with the body vessel. The loader assembly 500 advantageously allows the introduction of the delivery system 10 into the introducer sheath assembly 400 without substantial blood loss from the patient.

The prosthetic valve 11, balloon catheter 15 and delivery sleeve assembly 18 are advanced over the guide wire 14 through the introducer sheath, preferably as single unit, while tracking through the body vessel to the native valve site (see FIG. 1). In one advantageous feature, the delivery system 10 provides excellent pushability for facilitating advancement of the prosthetic valve 11 through the introducer sheath. In one embodiment, the delivery system 10 provides sufficient pushability to push through an introducer sheath having an inner circumference that is 2 French size smaller than outer circumferences of the valve 11 or shroud 200.

As the prosthetic valve 11 reaches the aortic arch 13 as shown in FIG. 1, the steerable function of the delivery system 10, described below, is actuated for facilitating advancement of the valve 11 around the arch. More particularly, the bending of the steerable section 20 assists in steering the valve 11 and/or the distal end 210 of the shroud 200 (see FIG. 14A) away from the inner surface of the aortic arch 13. As a result, retrograde advancement of the valve 11 around the aortic arch 13 may be achieved without damaging the aorta 13 or the valve 11. In one preferred delivery method, the valve is advanced over the aortic arch with little or no contact between the valve and the aorta.

In the illustrated embodiment, the steerable function of the delivery system 10 is accomplished as the operator rotates the rotator handle 28 (see FIG. 2). As the rotator handle 28 is rotated, the threaded portion 68 acts in conjunction with the exterior thread 54 of the partially threaded member 27 (see FIG. 4A), which does not rotate. The rotator handle 28 thus moves linearly relative to the partially threaded member 27. The first core member 26 also moves linearly relative to the partially threaded member 27 (see FIG. 2). The dowel 124 prevents relative rotation between the first core member 26 and the partially threaded member 27.

As the first core member 26 moves distally from the partially threaded member 27, the pull wire 312, connected to the first core member 26 by the ball bearing 122, exerts a force on the slot face 238 of the ring 202 (see FIG. 15A). The pull wire 312 draws the ring 202 toward the handle 22. The side of the delivery system 10 along which the pull wire 312 passes bends along the steerable section 20 as the elongate openings 166 of the flex tube 146 converge (see FIG. 11). The steerable section 20 bends until the pressure in the pull wire 312 is relieved. Additional rotation of the rotator handle 28 thus results in additional bending. The friction between the threaded portion 68 of the rotator handle 28 and the exterior thread 54 of the partially threaded member 27 (see FIGS. 4A and 5B) is sufficient to hold the pull wire 312 taut, thus preserving the shape of the bend in the steerable section 20 when the operator releases the rotator handle 28.

The natural rigidity of the cover 148 (see FIG. 10), as well as the natural rigidity of the balloon catheter 15 (see FIG. 16), act against the bending of the steerable section 20. The force on the pull wire 312 bends the steerable section 20, while the rigidity of the cover 148 and balloon catheter 15 described above resists the bending, thus "locking" the delivery system 10 in place over a range of positions from straight to fully curved, according to the rotation of the rotator handle 28. The cover 148 also protects the body vessel from the flex tube 146 (see FIG. 10), which absent the cover 148, may scrape or otherwise lacerate the body vessel.

As the balloon catheter 15 is advanced to the native valve site, the operator uses the marker bands 306, 308 (see FIG. 16) to identify the location of the valve 20, according to the process of fluoroscopy, which is well known in the art. The operator can adjust the position of the valve 11 by actuating the rotator handle 28 while holding the hub 30 stationary (see FIG. 2). Further control over valve position can be achieved by twisting the hub 30. The sleeve 19 is attached to the hub 30, and the delivery system 10 is sufficiently rigid to transmit the twisting movement to the distal end. Twisting motion is transferred through the steerable section 20 when the tube portions 174 of the flex tube 146 contact one another (see FIG. 11). Such contact can occur when the flex tube is fully bent, or can occur during twisting as the curved portions 170 of the elongate opening close such that the tube portions 174 contact one another.

The delivery sleeve assembly 18 (see FIG. 1) is at its most rigid when all of the remaining tube portions 174 of the flex tube 148 (see FIG. 11) are in contact with one another and the steerable section 20 is fully curved. In this position, the shape of the steerable section 20 preferably corresponds closely to the shape of the aortic arch 13 (as shown in FIG. 1) for ease of tracking. When pushing across the stenotic leaflets 12, the steerable section 20 is located in the ascending aorta of the patient, and the soft durometer section of the sleeve 19 flexes and bears against the aortic arch 13 (see FIG. 1), thereby preventing damage to the inner wall of the aorta.

After the delivery system 10 has been advanced such that the valve 11 is located adjacent to the native valve, the balloon catheter 15 may be distally advanced relative to the delivery sleeve assembly 18 to better position the valve 11 within the native leaflets. To accomplish this, the balloon catheter 15 is slidably advanced through the sleeve 19 and steerable section 20. In another advantageous feature, the delivery sleeve assembly 18 advantageously allows the physician to adjust the curvature of the steerable section 20 for properly aligning the prosthetic valve 11 with respect to the native valve. As a result, when the balloon catheter 15 is advanced distally, the prosthetic valve advances into the center of the native valve. Furthermore, the delivery system 10 provides sufficient pushability to push the balloon catheter 15 and valve 11 across the stenotic leaflets 12, or alternatively, to push the balloon catheter 15 across the stenotic leaflets 12. The shroud 200 (see FIG. 14A) may also cross the stenotic leaflets 12 during this process.

Figure 23:
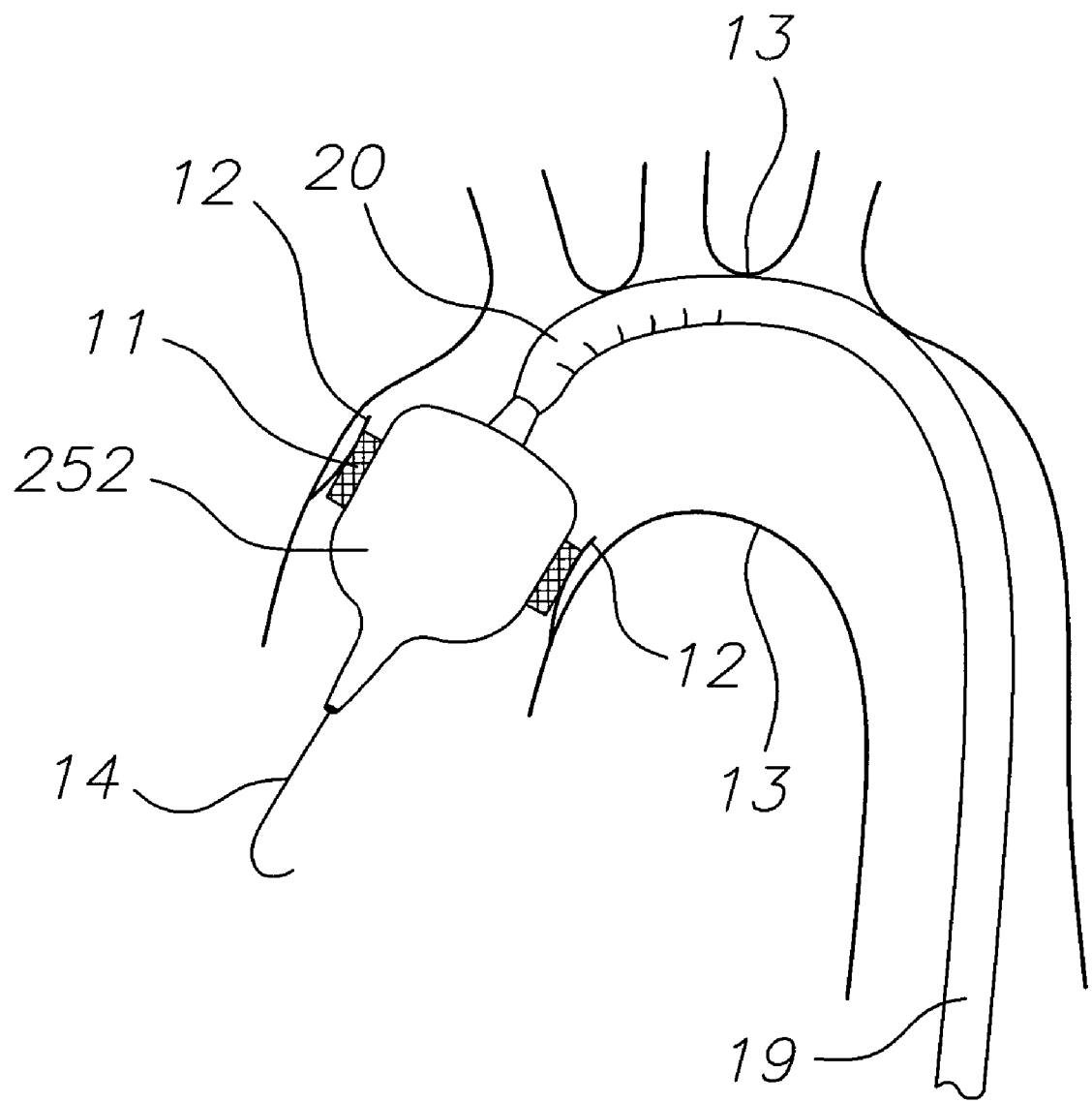
FIG. 23 is a side view of the delivery system during use, showing deployment of the prosthetic heart valve at the native valve site for replacing the function of a defective native valve.

Once the stenotic leaflets 12 have been pushed away, the delivery system 10 deploys the valve 11 in the native valve site, as shown in FIG. 23. The soft durometer section of the sleeve 19 bears against the aortic arch 13, while the steerable section 20 passes through the ascending aorta and is adjusted to position the valve 11. The valve 11 is balloon expandable and once positioned, the balloon 252 is inflated to secure the position of the valve 11 in the native valve site. The balloon 252 is then deflated, and the entire delivery system 10 is withdrawn as it passes back over the guide wire 14, and exits the body vasculature through the introducer sheath. The guide wire 14 is then withdrawn, followed by the introducer sheath.

In the alternative embodiment of the invention, wherein the valve 11 is placed inside the shroud 200, the delivery sleeve assembly 18 (see FIG. 1) is retracted once the valve 11 has reached the native valve site. The delivery sleeve assembly 18 is retracted as the operator holds the support 17 steady and pulls back (proximally) on the handle 22, which causes the delivery sleeve assembly 18 to retract proximally, exposing the valve 11 to the native valve site and allowing the balloon 252 to inflate as shown in FIG. 23, and thus deploy the valve 11 as described above.

It will be appreciated that embodiments of the heart valve delivery system 10 provide improved devices and methods for advancing a prosthetic heart valve through a patient's vasculature. In one preferred embodiment, the cooperation of components described herein allows an uncovered prosthetic valve to be advanced through the patient's vasculature and around the aortic arch in a safe manner. Accordingly, the delivery system enables advancement of a prosthetic valve around the aortic arch without requiring the introduction of an outer sheath into the aortic arch. This is an advantageous feature because the use of a sheath would increase the diameter of the delivery system, thereby complicating the delivery of the valve. In addition to providing an improved steering mechanism for navigating the aortic arch without damaging the inner wall of the aorta, it will be appreciated by those skilled in the art that the delivery system provides excellent pushability such that the physician has excellent control over the movement and location of the prosthetic valve during advancement into the native valve. This feature is particularly advantageous when traversing stenotic valve leaflets. Accordingly, embodiments of the present invention provide an improved delivery system for advancing a prosthetic valve to the site of a native aortic valve using a steerable assembly that eliminates the need for an outer sheath in the aorta, while providing sufficiently pushability to pass through narrow vasculature and/or stenotic valve leaflets. As a result, embodiments of the present invention provide improved devices and methods for percutaneously advancing a balloon-expandable prosthetic valve to the site of a stenotic aortic valve using a retrograde approach.

While the invention has been described in its preferred embodiments, it is to be understood that the words which have been used are words of description and not of limitation. Therefore, changes may be made within the scope of the appended claims without departing from the true scope and spirit of the invention.

What is claimed is:

1. A delivery system for deploying a prosthetic valve within a native aortic valve in a human heart, comprising:
    a tubular sleeve;
    a selectively steerable section permanently fixed to a distal end of the sleeve, the steerable section having a lumen with an inner diameter, the lumen communicating with an open distal end, the steerable section constructed to have a greater flexibility than the tubular sleeve;
    a pull wire permanently fixed to a distal end portion of the steerable section for selectively controlling a curvature of the steerable section, the steerable section capable of achieving sufficient curvature to navigate around an aortic arch;
    an elongate balloon catheter extending through the sleeve and through the lumen of the steerable section and out of the open distal end of the steerable section, the elongate balloon catheter being longitudinally movable relative to the sleeve and the steerable section; and
    a prosthetic valve disposed over an expandable balloon along a distal end portion of the elongate balloon catheter, the prosthetic valve having an outer diameter larger than the inner diameter of the steerable section such that the prosthetic valve is prevented from moving proximally through the steerable section when the balloon is deflated and the prosthetic valve is in a radially compressed state on the deflated balloon, the prosthetic valve comprising an expandable stent portion and a valve structure;
    wherein the sleeve, steerable section, balloon catheter and prosthetic valve are configured for advancement as a single unit through a patient's vasculature while the prosthetic valve is positioned distal to the steerable section and wherein the balloon catheter and prosthetic valve are movable in a distal direction relative to the sleeve and steerable section for implanting the prosthetic valve within a native aortic valve.

2. The delivery system according to claim 1 wherein the sleeve further comprises first and second outer lumens extending along a side of the sleeve.

3. The delivery system according to claim 2 wherein the pull wire passes through the first outer lumen, through the steerable section to the distal end portion of the steerable section, and returns through the steerable section and through the second outer lumen.

4. The delivery system according to claim 1 wherein the steerable section comprises a slotted tube having a first straight position and a second curved position.

5. The delivery system according to claim 1 wherein the sleeve is formed of a polyether block amide and wherein the sleeve comprises a soft durometer polyether block amide near a distal end thereof.

6. The delivery system according to claim 3 wherein the pull wire is actuated by a rotational handle assembly, wherein the rotational handle assembly is located proximal to the sleeve.

7. The delivery system according to claim 1 wherein the distal end portion of the steerable section abuts a proximal end of the prosthetic valve.

8. The delivery system according to claim 1 further comprising a shroud coupled to the distal end portion of the steerable section and wherein the shroud surrounds at least a portion of the prosthetic valve during advancement through the patient's vasculature.

9. The delivery system according to claim 1, wherein the steerable section comprises a flexible tubular portion and a cover extending over at least a portion of the tubular portion, the cover being less flexible than the tubular portion.

10. The delivery system of claim 1, wherein the pull wire has a proximal end portion connected to a handle mechanism, and a distal end portion connected to the steerable section, and wherein actuating the handle mechanism is effective to move the pull wire proximally to bend the steerable sector, while the sleeve undergoes substantially no deflection from the pull wire.

* * * * *